US012752131B2

(12) United States Patent
Ramezanzadeh Moghadam et al.

(10) Patent No.: US 12,752,131 B2
(45) Date of Patent: Oct. 6, 2026

(54) RADIOTHERAPY SYSTEMS AND METHODS FOR QUALITY ASSURANCE AND CALIBRATION

(71) Applicant: RefleXion Medical, Inc., Hayward, CA (US)

(72) Inventors: Amir Ramezanzadeh Moghadam, San Jose, CA (US); Thomas Leroy Laurence, Jr., Benicia, CA (US); David Quentin Larkin, Menlo Park, CA (US)

(73) Assignee: RefleXion Medical, Inc., Hayward, CA (US)

( * ) Notice: Subject to any disclaimer, the term of this patent is extended or adjusted under 35 U.S.C. 154(b) by 75 days.

(21) Appl. No.: 18/654,922

(22) Filed: May 3, 2024

(65) Prior Publication Data

US 2024/0359036 A1 Oct. 31, 2024

Related U.S. Application Data

(63) Continuation of application No. PCT/US2022/079175, filed on Nov. 2, 2022.

(Continued)

(51) Int. Cl.
*A61N 5/10* (2006.01)

(52) U.S. Cl.
CPC ......... *A61N 5/1071* (2013.01); *A61N 5/1081* (2013.01)

(58) Field of Classification Search
CPC ................ A61N 5/1071; A61N 5/1081; A61N 2005/1076; A61N 5/1075
See application file for complete search history.

(56) References Cited

U.S. PATENT DOCUMENTS 10,695,586 B2 6/2020 Harper et al.
10,702,715 B2 7/2020 Pearce et al.
(Continued)

FOREIGN PATENT DOCUMENTS

EP 2 708 919 A2 3/2014
WO WO 2016172352 A1 * 10/2016 ........... A61N 5/1049
(Continued)

OTHER PUBLICATIONS

International Search Report mailed on Feb. 23, 2023, for PCT Application No. PCT/US2022/079175, filed on Nov. 2, 2022, 5 pages.

(Continued)

*Primary Examiner* — Uzma Alam
*Assistant Examiner* — Richard O Toohey
(74) *Attorney, Agent, or Firm* — Cooley LLP

(57) ABSTRACT

Disclosed herein are systems and methods for measuring the radiation emitted from the therapeutic radiation source. One variation of a radiotherapy system includes a radiation measurement device that is coupled to a radiotherapy system housing. The radiation measurement device may be movably coupled to the housing, and its position and/or motion is independent from the position and/or motion of the therapeutic radiation source. In one variation, the radiation measurement device is at a location on the system housing where it may measure exit beams with little or no interference with entrance beams. Also disclosed herein are radiotherapy systems that include one or more radiopaque or radiation emitting fiducials coupled to the housing.

33 Claims, 19 Drawing Sheets

Related U.S. Application Data

(60) Provisional application No. 63/275,323, filed on Nov. 3, 2021.

(56) References Cited

U.S. PATENT DOCUMENTS

| | | | | |
|---|---|---|---|---|
| 2015/0283403 | A1* | 10/2015 | Kapatoes | A61N 5/1071 600/1 |
| 2018/0185672 | A1 | 7/2018 | Ramezanzadeh Moghadam | |
| 2020/0061391 | A1* | 2/2020 | Krishnaswamy | A61N 5/1071 |
| 2023/0173305 | A1* | 6/2023 | Roberts | G01T 1/22 250/252.1 |
| 2025/0332449 | A1 | 10/2025 | Sun | |

FOREIGN PATENT DOCUMENTS

| | | | |
|---|---|---|---|
| WO | WO-2021/007459 | A1 | 1/2021 |
| WO | WO-2022/036707 | A1 | 2/2022 |
| WO | WO-2022/144538 | A1 | 7/2022 |

OTHER PUBLICATIONS

International Search Report mailed on Jun. 6, 2024, for PCT Application No. PCT/US2023/085347, filed on Dec. 21, 2023, 6 pages.

Islam, M.K. et al. (Dec. 2009). "An integral quality monitoring system for real-time verification of intensity modulated radiation therapy," Med. Phys. 36(12):5420-5428.

Müller, L. (May 2018). "Maritimes an der Waterkant: Neues von Dolphin & Compass," Dosimetry, iba Group, located at https://www.uke.de/extern/akimrt/Download/180528Hamburg/180528Mo05mueller.pdf, retrieved on Jul. 19, 2024, 53 pages.

Nicolini, G. et al. (Sep. 2008). "The GLAaS algorithm for portal dosimetry and quality assurance of RapidArc, an intensity modulated rotational therapy," Radiat. Oncol. 3:24, 10 pages.

Samant, S.S. et al. (Dec. 2002). "Verification of multileaf collimator leaf positions using an electronic portal imaging device," Med. Phys. 29(12):2900-2912.

Written Opinion of the International Searching Authority mailed on Jun. 6, 2024, for PCT Application No. PCT/US2023/085347, filed on Dec. 21, 2023, 10 pages.

Written Opinion of the International Searching Authority mailed on Feb. 23, 2023, for PCT Application No. PCT/US2022/079175, filed on Nov. 2, 2022, 7 pages.

Moustakis, C. et al. (Jan. 2020). "A novel approach to SBRT patient quality assurance using EPID-based real-time transit dosimetry," Strahlenther Onkol. 196:182-192.

* cited by examiner

RADIOTHERAPY SYSTEMS AND METHODS FOR QUALITY ASSURANCE AND CALIBRATION

CROSS-REFERENCE TO RELATED APPLICATIONS

This application is a continuation of International Patent Application No. PCT/US2022/079175, filed Nov. 2, 2022, which claims priority to U.S. Provisional Patent Application Ser. No. 63/275,323 filed Nov. 3, 2021, which is hereby incorporated by reference in its entirety.

BACKGROUND

Radiotherapy aims to deliver a prescribed dose of radiation to tumor(s) while limiting the irradiation of surrounding healthy tissue. Radiotherapy systems are precision machines that have a therapeutic radiation source that generates radiation, and a collimation assembly that precisely shapes that radiation. The therapeutic radiation source is mounted on a motion system, such as an arm or a circular gantry, that moves it around the patient so that radiation can be delivered from various firing positions (e.g., firing angles) to irradiate tumors and avoid radiation-sensitive structures (e.g., organs-at-risk or OARs). The radiation fluence emitted by the therapeutic radiation source is calculated during radiotherapy treatment planning. A radiotherapy treatment plan generates a fluence map that specifies the amount of radiation to be emitted from a plurality of firing positions during a treatment session.

Although the fluence map from radiotherapy treatment planning specifies the fluence to be emitted, the actual dose delivered may differ from the plan due to variabilities in the radiotherapy system itself. Such variabilities may emerge from the radiation beam emitted by the therapeutic radiation source, the collimation assembly, and/or any effect on the therapeutic radiation source and/or collimation assembly as the motion system changes the position of the therapeutic radiation source. For example, in a motion system that is configured to rotate the therapeutic radiation source around the patient area, the quality of the beam (e.g., homogeneity of the irradiation field) and/or the ability of the collimation assembly to shape the beam may be impacted depending on their orientation. Moreover, these variabilities may be unique to each radiotherapy system, and careful procedures are undertaken to characterize the variabilities of radiotherapy system components individually and working together. Quality assurance (QA) tests are conducted to ensure that the system operates within accepted safety ranges.

Therefore, it is desirable to have methods and devices on the radiotherapy system that can help facilitate the process of QA testing and calibration of one or more components of a radiotherapy system, as well as help evaluate the performance of radiation delivery.

SUMMARY

Disclosed herein are systems and methods for measuring the radiation emitted from a therapeutic radiation source and calibrating the MV detector of a radiotherapy system. One variation of a radiotherapy system comprises a radiation measurement device that is coupled to (e.g., integrated, embedded, etc.) a radiotherapy system housing, e.g., the surface of the housing. The radiation measurement device may be movably coupled to the housing, and its position and/or motion is independent from the position and/or motion of the therapeutic radiation source. In one variation, the radiation measurement device may be at a location on the system housing where it may measure exit beams (e.g., the radiation emanating from a patient area of the radiotherapy system) with little or no interference with entrance beams (e.g., the radiation that is emitted toward the patient area). A radiotherapy system may comprise one or more radiopaque fiducials coupled to the housing surface. For example, a radiotherapy system may comprise a plurality of radiopaque fiducials distributed around a perimeter of the housing surface.

Also disclosed herein are methods for calibrating an MV detector located opposite (or coplanar with) the therapeutic radiation source using a radiation measurement device that has a position and/or motion that is de-coupled from the position and/or motion of the therapeutic radiation source.

One variation of a radiotherapy system may include a gantry that is rotatable about a patient area, a therapeutic radiation source mounted on the rotatable gantry, a housing disposed over the rotatable gantry, and a radiation fluence measurement device that is coupled to a surface of the housing. Alternatively, in another variation, the radiation fluence measurement device may be coupled to any radiotherapy system component that does not move in synchronicity with the therapeutic radiation source. The radiation fluence measurement device may be movable independently of the therapeutic radiation source. In one example, the radiation fluence measurement device may be movable along the housing surface. The radiation fluence measurement device may be laterally (e.g., along an axis that is perpendicular to the axis of rotation of the gantry, an X-axis, an IEC-X axis) movable along the housing surface or may be in a fixed location along the housing surface. The radiation fluence measurement device may be located on the housing surface such that it measures radiation exiting the patient area. The radiation fluence measurement device may be located on the housing surface such that it does not interfere with a therapeutic radiation beam directed at the patient area. The radiotherapy system may further include a bore defined by the housing surface and have a longitudinal axis, where the radiation fluence measurement device may be offset from the therapeutic radiation source along the longitudinal axis. In another variation, a radiotherapy system may include a bore defined by the housing surface and have a longitudinal axis, where the therapeutic radiation source may be located at a first position along the longitudinal axis and the radiation fluence measurement device may be located at a second position along the longitudinal axis at an offset distance from the first position. The offset distance may be at least about 0.4 cm, e.g., at least about 0.5 cm, at least about 0.7 cm, at least about 0.8 cm. In some variations, the offset distance may be greater than or equal to half a radiation field size at the housing surface. The radiotherapy system may also include a radiation imaging detector mounted on the gantry directly opposite the therapeutic radiation source and/or an imaging system mounted on the rotatable gantry. The imaging system may include a CT imaging system and/or a PET imaging system. The radiation fluence measurement device may include one or more of an ion chamber, diode array, dosimetry film, thin film transistor (TFT), thermoluminescent dosimeter (TLD), and/or a dosimeter. The gantry may be continuously rotatable through 360°. The radiation fluence measurement device may be coupled to a surface of the housing at a location determined based on a radiotherapy treatment plan fluence map. In some variations, the housing includes a bore tube and the radiation fluence measurement device may be coupled to a surface of the bore tube.

Some variations of a radiotherapy system may further include a first radiation fluence measurement device and a second radiation fluence measurement device. The second radiation fluence measurement device may be coupled to the housing surface opposite the first radiation fluence measurement device. For example, the second radiation fluence measurement device may be coupled to the housing surface about 90° from the first radiation fluence measurement device. In a radiotherapy system that includes a bore defined by the housing surface and has a longitudinal axis, the therapeutic radiation source may be located at a first position along the longitudinal axis, the first radiation fluence measurement device may be located at a second position along the longitudinal axis at an offset distance from the first position, and the second radiation fluence measurement device may be located at a third position along the longitudinal axis at a second offset distance from the first position. For example, the second radiation fluence measurement device may be axially adjacent to the first radiation fluence measurement device. Some variations may further include a radiopaque fiducial coupled to the housing surface. A radiotherapy system may include a plurality of radiopaque fiducials distributed around a perimeter of the housing surface that defines the bore. Each of the plurality of radiopaque fiducials may be uniquely identifiable from the others. In some variations, the plurality of radiopaque fiducials may be distributed around the perimeter of a cross-section of the bore, where the cross-section may be located at a second offset distance from the first position, e.g., the second offset may be at least about 0.4 cm and/or may be greater than or equal to half a radiation field size at the housing surface. The plurality of radiopaque fiducials may be located on the housing surface such that the fiducials do not interfere with a therapeutic radiation beam directed at the patient area.

Also described herein are methods for measuring radiation fluence from a radiation source (e.g., a therapeutic radiation source). One variation of a method may include emitting radiation from the radiation source (e.g., a therapeutic radiation source) toward a patient area while the radiation source is rotated about the patient area by a gantry, where the gantry has a rotatable portion to which the radiation source is mounted and a stationary frame, and measuring the emitted radiation using a radiation fluence measurement device that may be coupled to a surface of a housing disposed over the gantry and/or the stationary frame. Alternatively, in another variation, the radiation fluence measurement device may be coupled to any radiotherapy system component that does not move in synchronicity with the therapeutic radiation source. The radiation fluence measurement device may be stationary relative to the rotatable gantry. In some examples, the radiation fluence measurement device may be movable independently of the radiation source. The radiation fluence measurement device may be located on the housing surface such that it does not interfere with the radiation emitted toward the patient area. In some variations, the radiation fluence measurement device may be located on the housing surface such that it measures radiation exiting the patient area. Rotating the gantry may move the radiation source along a circular trajectory, and measuring the emitted radiation may include acquiring measurements using the radiation fluence measurement device when the radiation source is at a location on the circular trajectory that is furthest from the radiation fluence measurement device. Measuring the emitted radiation using the radiation fluence measurement device may include acquiring radiation fluence measurements for each of a plurality of radiation source locations. In some variations, a method may further include placing an object (e.g., a phantom) with prespecified geometric and material properties in the patient area. The object may include one or more of water and/or slabs of plastic, and/or portions with homogeneous material properties, and/or portions with inhomogeneous material properties, and/or a portion with varying heights. For example, the portion with varying heights may be a stepped wedge.

In some variations, a multi-leaf collimator (MLC) may be located in a radiation path of the radiation source and configured to shape the emitted radiation. The MLC may include a plurality of MLC leaves that are movable to various MLC configurations. The method may further include changing the MLC configuration, and where measuring the emitted radiation may include acquiring measurements for the changed MLC configuration. In some variations, the method may further include changing the MLC configuration to change a field size of the emitted radiation, emitting radiation with a changed field size, and measuring the emitted radiation with the changed field size. Some methods may include measuring the emitted radiation using a non-calibrated detector and calibrating the non-calibrated detector based on the measurements from the radiation fluence measurement device and the non-calibrated detector. The imaging system may include an MV detector and the acquired imaging data may include MV detector imaging data. Alternatively, or additionally, the imaging system may include a PET imaging system and the acquired imaging data may include PET imaging data. In some variations, the emitted radiation may include scattered radiation and the radiation fluence measurement device may be coupled to the housing surface at a location such that it measures scattered radiation. The housing may include a bore tube and the radiation fluence measurement device may be coupled to a surface of the bore tube.

Also disclosed herein are methods for evaluating radiation delivery. One variation of a method may include calculating an expected fluence level for a measurement device at a specified location during radiation delivery according to a radiotherapy treatment plan, emitting radiation according to the radiotherapy treatment plan, measuring a delivered level of the emitted radiation using the fluence measurement device at the specified location, comparing the delivered fluence level with the expected fluence level, and generating a notification that indicates whether the delivered fluence level is within an acceptable tolerance of the expected fluence level. Emitting radiation may include emitting radiation using a therapeutic radiation source of a radiotherapy system. The radiotherapy system may include a rotatable gantry to which the therapeutic radiation source may be mounted, a housing disposed over the rotatable gantry, and the fluence measurement device, where the fluence measurement device may be coupled to a surface of the housing. The radiation fluence measurement device may be movable independently of the therapeutic radiation source. The radiation fluence measurement device may be located, for example, on the housing surface such that it does not interfere with a radiation beam directed at a patient area of the radiotherapy system. In some variations, the radiotherapy system may further include a bore defined by the housing surface and having a longitudinal axis, where the radiation fluence measurement device may be offset from the therapeutic radiation source along the longitudinal axis. The radiotherapy system may further include a bore defined by the housing surface and having a longitudinal axis. The therapeutic radiation source may be located at a first position along the longitudinal axis and the radiation fluence measurement device may be located at a second position along the longitudinal axis at an offset distance from the first position. For example, the offset distance may be at least about 0.4 cm. In some variations, the method may further include calculating a second expected fluence level for a second fluence measurement device at a second specified location during radiation delivery according to a radiotherapy treatment plan, measuring a second delivered fluence level of the emitted radiation using the second fluence measurement at the second specified location, comparing the second delivered fluence level with the second expected fluence level, and generating a notification that indicates whether the second delivered fluence level is within an acceptable tolerance of the second expected fluence level.

DETAILED DESCRIPTION

Figure 1A:
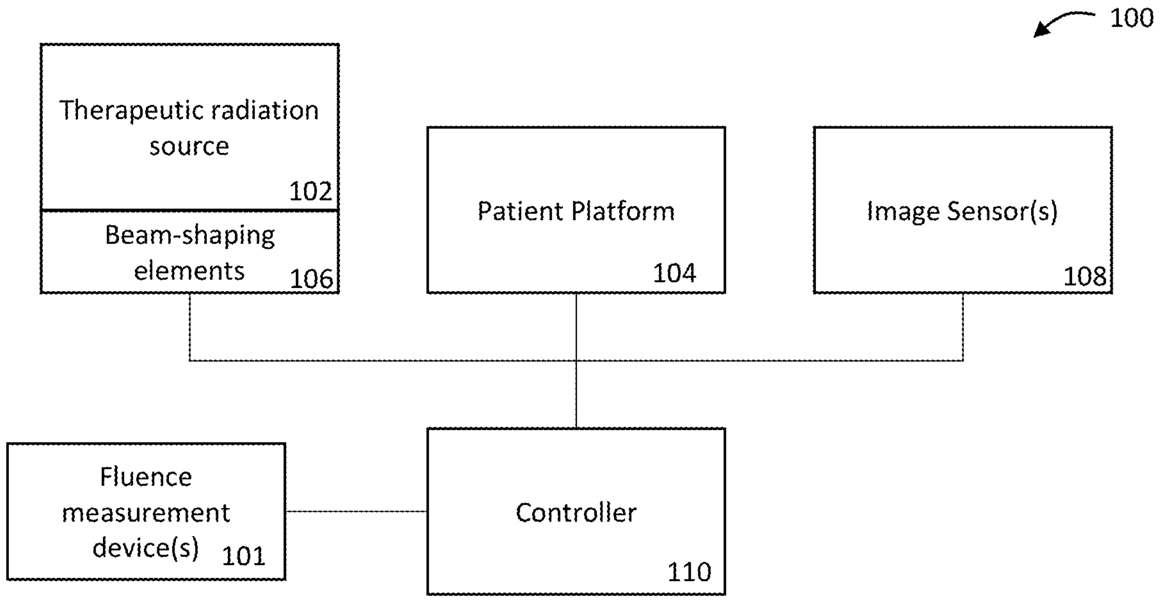
FIG. 1A is a block diagram of an illustrative variation of a radiotherapy system.

Radiotherapy systems comprise a therapeutic radiation source that is used to deliver high doses of radiation to irradiate a tumor. In some variations, the therapeutic radiation source may comprise a high-energy photon source (such as a linear accelerator or linac) and an MV detector that may be used to measure the radiation emitted by the therapeutic radiation source. The MV detector measurements may be used to determine whether the radiation emitted by the therapeutic radiation source matches (or approximates within an acceptable tolerance) the planned radiation dose. However, the MV detector may not provide a complete measurement of the exit radiation. MV detectors may be sensitive to the radiation spectrum as well as to the scattered radiation from surrounding objects and therefore may not accurately measure exit radiation. Although the radiation emitted by the linac toward the patient area of the radiotherapy system may have a certain energy spectrum, after the radiation has interacted with a patient and/or object (e.g., phantom) in the patient area, the radiation spectrum may vary due to differing levels of absorption, reflection, and/or transmission of the radiation through the patient and/or object. The radiation exiting the patient area may have a different energy spectrum and/or may be scattered in different directions. An MV detector that is calibrated to detect a certain range of radiation energy levels may not provide an accurate measurement of radiation that is outside of that range. The systems described herein may comprise fluence measurement devices coupled to a radiotherapy system such that they may facilitate the measurement of radiation emitted to the patient area. The fluence measurement devices may not be spectrally sensitive and may be configured to detect radiation of a broader spectrum than the MV detector.

The radiotherapy systems described herein may comprise a system housing that comprises a wall that defines a bore, and the one or more radiation fluence measurement devices may be coupled to the surface of the system housing along the bore. For example, at least one radiation fluence measurement device may be mounted to and/or embedded into the bore wall. In some variations, a radiation fluence measurement device may be coupled to the radiotherapy system at a location that allows it to sample exit radiation (i.e., radiation emanating outward from the patient area) without interfering with the entrance radiation (i.e., radiation directed toward the patient area). A radiation fluence measurement device that interferes with the entrance radiation may affect the amount of radiation delivered to the patient area. For example, a fluence measurement device located within the entrance radiation or entrance beam may reduce the amount of radiation emitted to the patient area and/or may introduce additional radiation scatter, which may negatively impact the precision with which the entrance beam irradiates a patient. The one or more radiation fluence measurement devices described herein may comprise one or more of an ion chamber, a diode array, thin film transistor (TLT), thermoluminescent dosimeter (TLD), film, and/or any radiation photon detection device and/or combinations of the foregoing. In some variations, an anti-backscatter plate may be located behind a radiation fluence measurement device to absorb backscattered radiation that may cause measurement artifacts. For example, an anti-backscatter plate may comprise a plate made of one or more of tungsten, lead, copper, iron, steel, and/or aluminum, e.g., a 5 mm thick tungsten plate.

Some variations of a radiotherapy system may comprise one or more radiation fluence measurement devices whose location and/or motion are independent from the location and/or motion of the therapeutic radiation source. That is, a change in the location and/or motion of the therapeutic radiation device does not necessitate a change in the location and/or motion of the fluence measurement device(s). In some variations, the one or more radiation fluence measurement devices may be stationary and coupled to the system housing such that its position does not change after it has been installed, regardless of the location and/or motion of the therapeutic radiation source. In other variations, the one or more radiation fluence measurement devices may be movably coupled to the system housing. For example, the fluence measurement device may be laterally movable along the housing surface. The motion range of the fluence measurement device may be selected such that the fluence measurement device can measure the exit beam with little or no interference of the entrance beam. The location and/or motion of the radiation fluence measurement device may be controlled by a system controller. The location and/or motion of the therapeutic radiation source may also be controlled by the system controller, and may be de-coupled from the location and/or motion of the fluence measurement device. For example, there may be a mode of operation where the motion of the fluence measurement device may not be synchronized and/or coordinated with the motion of the therapeutic radiation source.

Some variations of a radiotherapy system may further comprise one or more radiopaque fiducials coupled to a housing surface. In some variations, the radiopaque fiducial may be embedded in the housing surface of the radiotherapy system. In some variations, the radiopaque fiducials may be coupled to the housing surface in a location such that they do not interfere with the entrance beam. The radiopaque fiducial(s) may facilitate the evaluation of the position and/or orientation and/or alignment of the radiotherapy system components.

Radiotherapy System

FIG. 1A depicts a functional block diagram of a variation of a radiotherapy system. Radiotherapy system (100) comprises one or more therapeutic radiation sources (102) and a couch or patient platform (104). The therapeutic radiation source may comprise an X-ray source, electron source, proton source, and/or a neutron source. For example, a therapeutic radiation source (102) may comprise a linear accelerator (linac), Cobalt-60 source, and/or an X-ray machine. The therapeutic radiation source may be movable about the patient platform so that radiation beams may be directed to a patient on the patient platform from multiple firing positions and/or angles. In some variations, a radiotherapy system may comprise one or more beam-shaping elements and/or assemblies (106) that may be located in the beam path of the therapeutic radiation source. For example, a radiotherapy system may comprise a linac (102) and a beam-shaping assembly (106) disposed in a path of the radiation beam. The beam-shaping assembly may comprise one or more movable jaws and one or more collimators. At least one of the collimators may be a multi-leaf collimator (e.g., a binary multi-leaf collimator, a 2-D multi-leaf collimator, etc.). The linac and the beam-shaping assembly may be mounted on a gantry or movable support frame that comprises a motion system configured to adjust the position of the linac and the beam-shaping assembly. In some variations, the linac and beam-shaping assembly may be mounted on a support structure comprising one or more robotic arms, C-arms, gimbals, and the like. The patient platform (104) may also be movable. For example, the patient platform (104) may be configured to translate a patient linearly along a single axis of motion (e.g., along the IEC-Y axis), and/or may be configured to move the patient along multiple axes of motion (e.g., 2 or more degrees of freedom, 3 or more degrees of freedom, 4 or more degrees of freedom, 5 or more degrees of freedom, etc.). In some variations, a radiotherapy system may have a patient platform with multiple degrees of freedom (e.g., 5-DOF, 6-DOF) that is configured to move along the IEC-Y axis, the IEC-X axis, the IEC-Z axis, as well as pitch, roll, and/or yaw.

The radiotherapy systems described herein may also comprise one or more fluence measurement devices (101). The one or more fluence measurement devices (101) may be coupled to the housing or covers of the radiotherapy system. In some variations, the fluence measurement device(s) may be movable independently of the motion and/or position of the therapeutic radiation device. The fluence measurement device(s) may be at a location on the system housing such that it may measure radiation exiting the patient area with little or no interference with the radiation directed at the patient area. Optionally, some radiotherapy systems may comprise one or more radiopaque fiducials coupled to the system housing. The fluence measurement device(s) and fiducial(s) are described further below.

A radiotherapy system (100) may comprise a controller (110) that is in communication with the therapeutic radiation source (102), beam-shaping elements or assemblies (106), patient platform (104), one or more image sensors (108) (e.g., one or more imaging systems), and the one or more fluence measurement devices (101). The controller (110) may comprise one or more processors and one or more machine-readable memories in communication with the one or more processors, which may be configured to execute or perform any of the methods described herein. The controller may record and store information generated during the delivery of radiation treatment including beam energy, monitor units, MLC and couch data, images taken during delivery, etc. in the machine-readable memory. The one or more machine-readable memories may store instructions to cause the processor to execute modules, processes and/or functions associated with the system, such as one or more treatment plans, system calibration procedures, system quality assurance (QA) procedures, the calculation of radiation fluence maps based on treatment plan and/or clinical goals, segmentation of fluence maps into radiotherapy system instructions (e.g., that may direct the operation of the gantry, therapeutic radiation source, beam-shaping assembly, patient platform, and/or any other components of a radiotherapy system), iterative calculations for updating the location(s) of a target region, and image and/or data processing associated with treatment planning and/or radiation delivery. In some variations, the memory may store treatment plan data (e.g., treatment plan firing filters, fluence map, planning images, treatment session PET pre-scan images and/or initial CT, MRI, and/or X-ray images). In some variations, the controller may be configured to compare data acquired during radiation delivery with treatment plan data to evaluate how closely the actual radiation delivery matched the planned radiation delivery (e.g., a "record and verify" system). The controller of a radiotherapy system may be connected to other systems by wired or wireless communication channels. For example, the radiotherapy system controller may be in wired or wireless communication with a radiotherapy treatment planning system controller such that fluence maps, firing filters, initial and/or planning images (e.g., CT images, MRI images, PET images, 4-D CT images), patient data, and other clinically-relevant information may be transferred from the radiotherapy treatment planning system to the radiotherapy system. The delivered radiation fluence, any dose calculations, and any clinically-relevant information and/or data acquired during the treatment session may be transferred from the radiotherapy system to the radiotherapy treatment planning system. This information may be used by the radiotherapy treatment planning system for adapting the treatment plan and/or adjusting delivery of radiation for a successive treatment session. Additional description of radiotherapy systems will be provided below and are also provided in U.S. Pat. No. 10,695,586 filed Nov. 15, 2017, which is hereby incorporated by reference in its entirety.

Figure 1B:
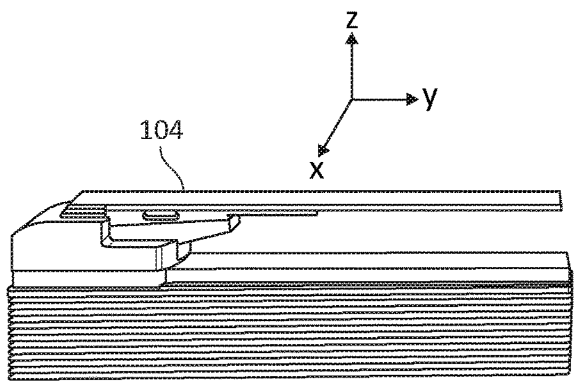
FIG. 1B is a side view of an illustrative variation of a radiotherapy system.
Figure 1B:
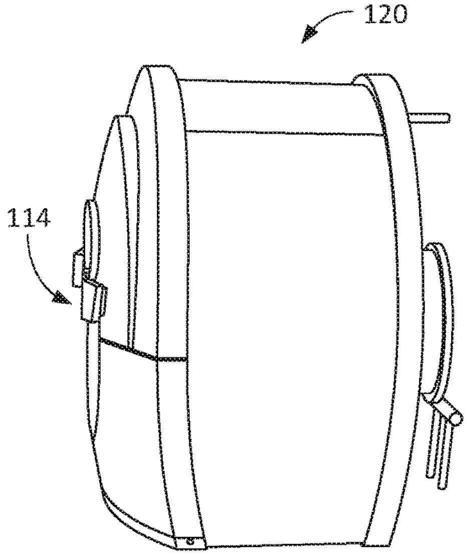
Figure 1C:
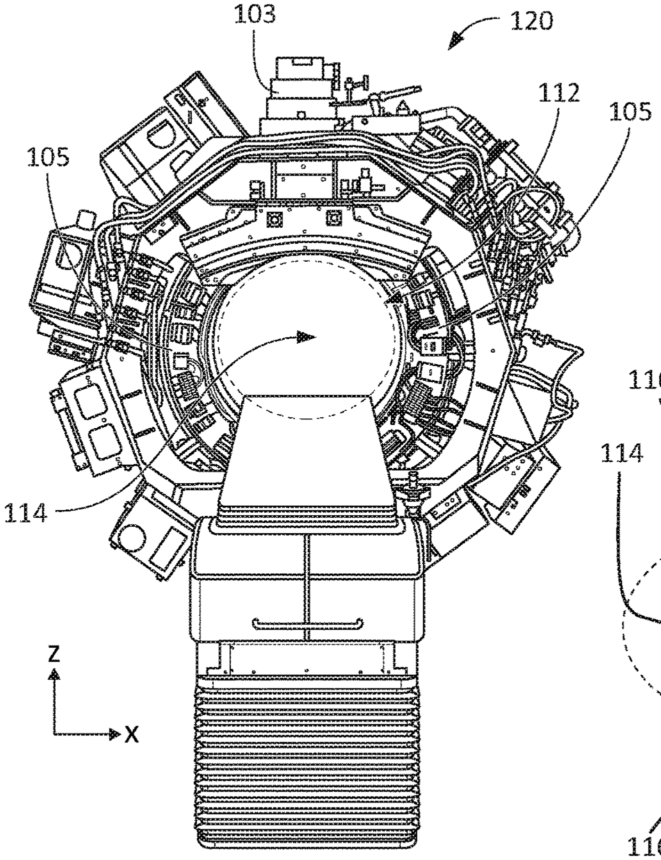
FIG. 1C is a front view of an illustrative variation of a radiotherapy system.

FIGS. 1B and 1C depict one example of a radiotherapy system (120) comprising a therapeutic radiation source (e.g., linac 103) mounted on a circular (e.g., ring) gantry and an MV detector mounted on the circular gantry directly opposite (i.e., 180 degree across from) the therapeutic radiation source (103). FIG. 1B depicts a side view of the radiotherapy system (120) with the system covers (also referred herein as the system housing), and FIG. 1C depicts a front view of the radiotherapy system without the system covers. The radiotherapy system (120) may optionally comprise two PET arcs (105, 107) located opposite each other on the gantry. In some variations, the PET arcs may not be located within the irradiation field of the therapeutic radiation source. For example, the PET arcs may be about 90 degrees offset from the linac (103) and MV detector. The central opening of the gantry may comprise a bore (114). In some variations, the system covers may comprise front covers, rear covers, and a bore tube surrounding the bore. For example, FIG. 1E depicts a radiotherapy system bore tube (115) having bore walls (116). A bore tube may be comprised of materials that are different from the materials of the other system covers. In some variations, a bore tube may comprise materials that have low radiation scattering properties and/or high radiation transmission properties. While the depicted radiotherapy system is an open-bore system, in other variations, the radiotherapy system may be a closed-bore system or any radiotherapy system having system housing or covers that comprise a bore tube. The surface of the bore tube may comprise the bore wall. The radiotherapy system may comprise a patient area (112) which refers to a region within the bore where a patient may be located for a treatment and/or imaging session. For example, the patient may be positioned on the patient platform (104), which may then move the patient into the patient area. It should be understood that in some variations of non-therapeutic procedures, a phantom and/or fluence measurement devices may be placed in the patient area instead of a patient. For example, during a quality assurance (QA) and/or system testing procedure, one or more phantoms and/or fluence measurement devices may be positioned on the patient platform (104) and moved into the patient area (112).

Throughout this description, radiation that is directed toward and/or into the patient area is referred to as an entrance beam or entrance radiation. FIG. 1F is a schematic depiction of various illustrative entrance beams or entrance radiation (130) to a patient area (112). An entrance beam or entrance radiation may refer to radiation that is directed into (e.g., moves toward, enters) the patient area. In contrast, an exit beam or exit radiation may refer to radiation that leaves (e.g., moves away from, exits) the patient area, including radiation emitted by the therapeutic radiation source that has interacted with a patient (and/or phantom and/or fluence measurement device) in the patient area. FIG. 1G is a schematic depiction of various illustrative exit beams or exit radiation (140) to a patient area (112).

Figure 1D:
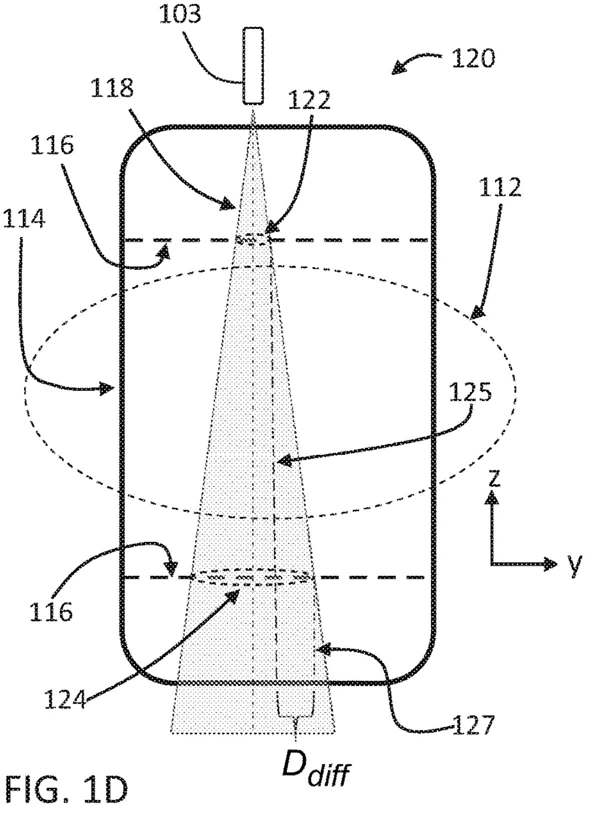
FIG. 1D depicts a cross-sectional view of an illustrative variation of a radiotherapy system.
Figure 1E:
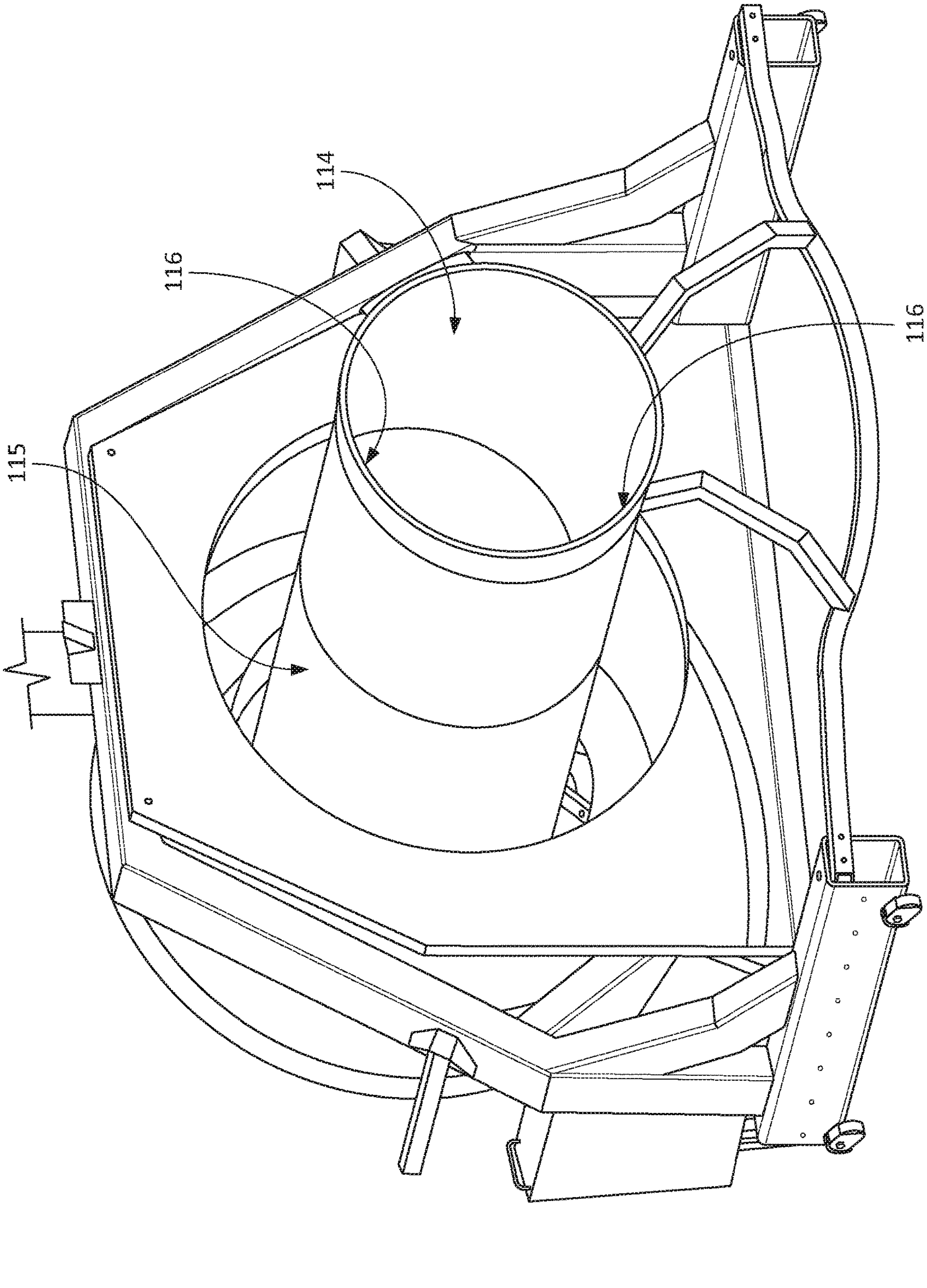
FIG. 1E depicts one variation of a radiotherapy system bore tube.
Figure 1F:
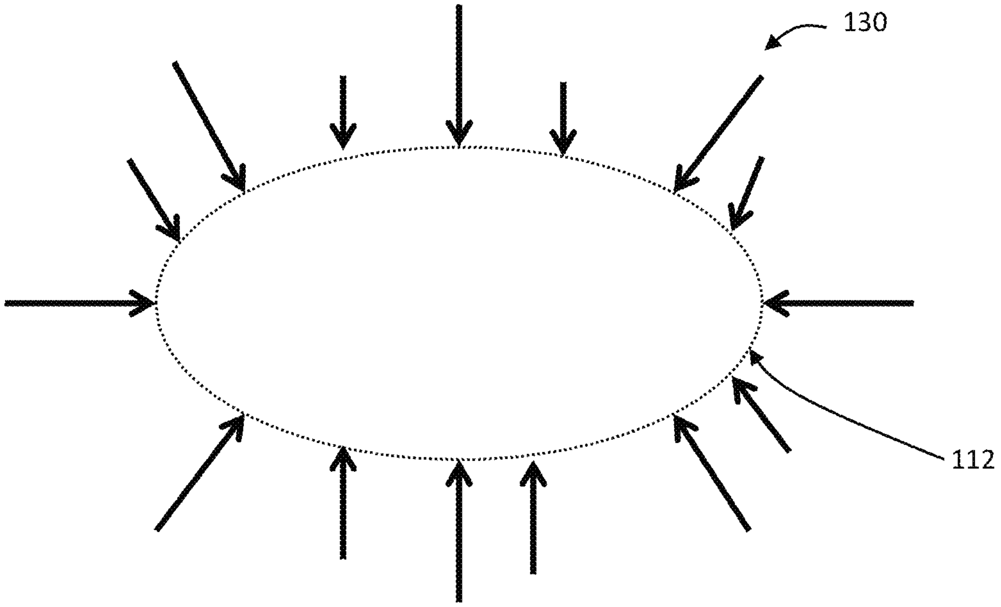
FIGS. 1F and 1G depict schematic depictions of entrance beams and exit beams, respectively.
Figure 1G:
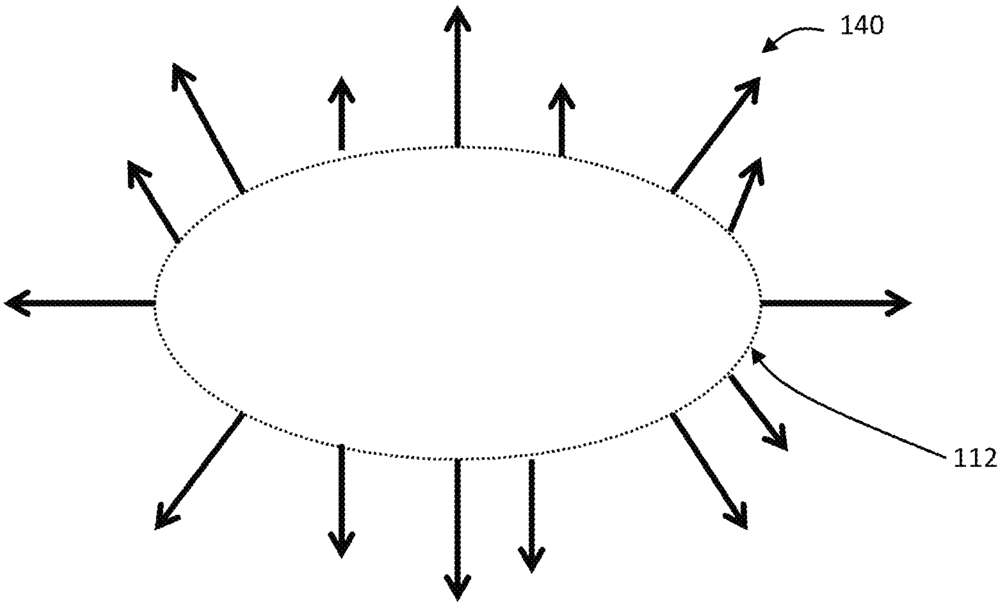

FIG. 1D depicts a schematic side cross-sectional view of radiotherapy system (120), depicting the linac (103), and the bore (114), which is defined by bore walls (116) of a bore (e.g., a bore tube similar to that depicted in FIG. 1E). The linac (103) may be configured to emit an entrance radiation beam (118) toward the patient area (112). As depicted in FIG. 1D, the radiation beam (118) may intersect with the region of the bore wall closest to the linac at an entrance irradiation field (122) and may also intersect with the region of the bore wall furthest from the linac at an exit irradiation field (124). In other words, the entrance beam has the entrance irradiation field (122) at the bore wall closest to the linac and the exit beam has the exit irradiation field (124) at the bore wall furthest from the linac. The projection of the entrance irradiation field (122) and exit irradiation field (124) on the bore wall may have any shape. For illustrative purposes, the entrance and exit irradiation fields may be depicted herein as being circular, however, in other variations, the entrance and exit irradiation fields may have any other shape, e.g., rectangular, slit-like, etc. The largest dimension of the entrance irradiation field (122) is smaller than the largest dimension of the exit irradiation field (124). For example, a circular entrance irradiation field (122) may have a diameter of $d_{entrance}$ and a corresponding circular exit irradiation field (124) may have a diameter of $d_{exit}$, where $d_{exit} > d_{entrance}$. In FIG. 1D, the dotted line (125) indicates the edge of the entrance irradiation field (122) projected onto the exit irradiation field (124). The dotted line (127) indicates the edge of the exit irradiation field (124). The difference between the edge of the entrance irradiation field (122) and the edge of the exit irradiation field (124) is a distance $D_{diff}$. In some variations, one or more fluence measurement devices (not shown in FIG. 1D) may be coupled to the bore wall within the region specified by the distance $D_{diff}$, i.e., outside the entrance irradiation field but within the exit irradiation field.

Figure 2A:
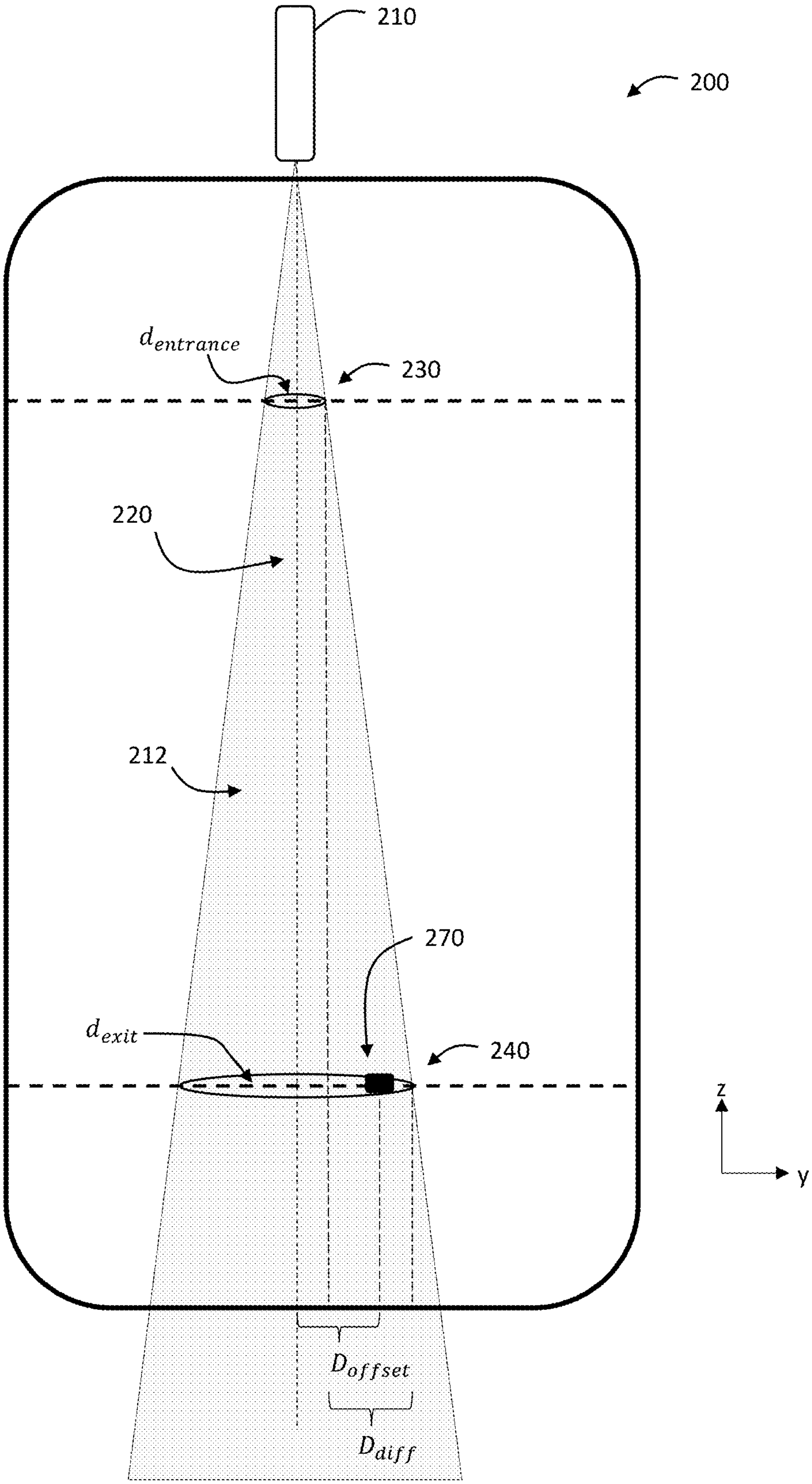
FIGS. 2A-2B depict a side cross-sectional view of an illustrative variation of a radiotherapy system.
Figure 2B:
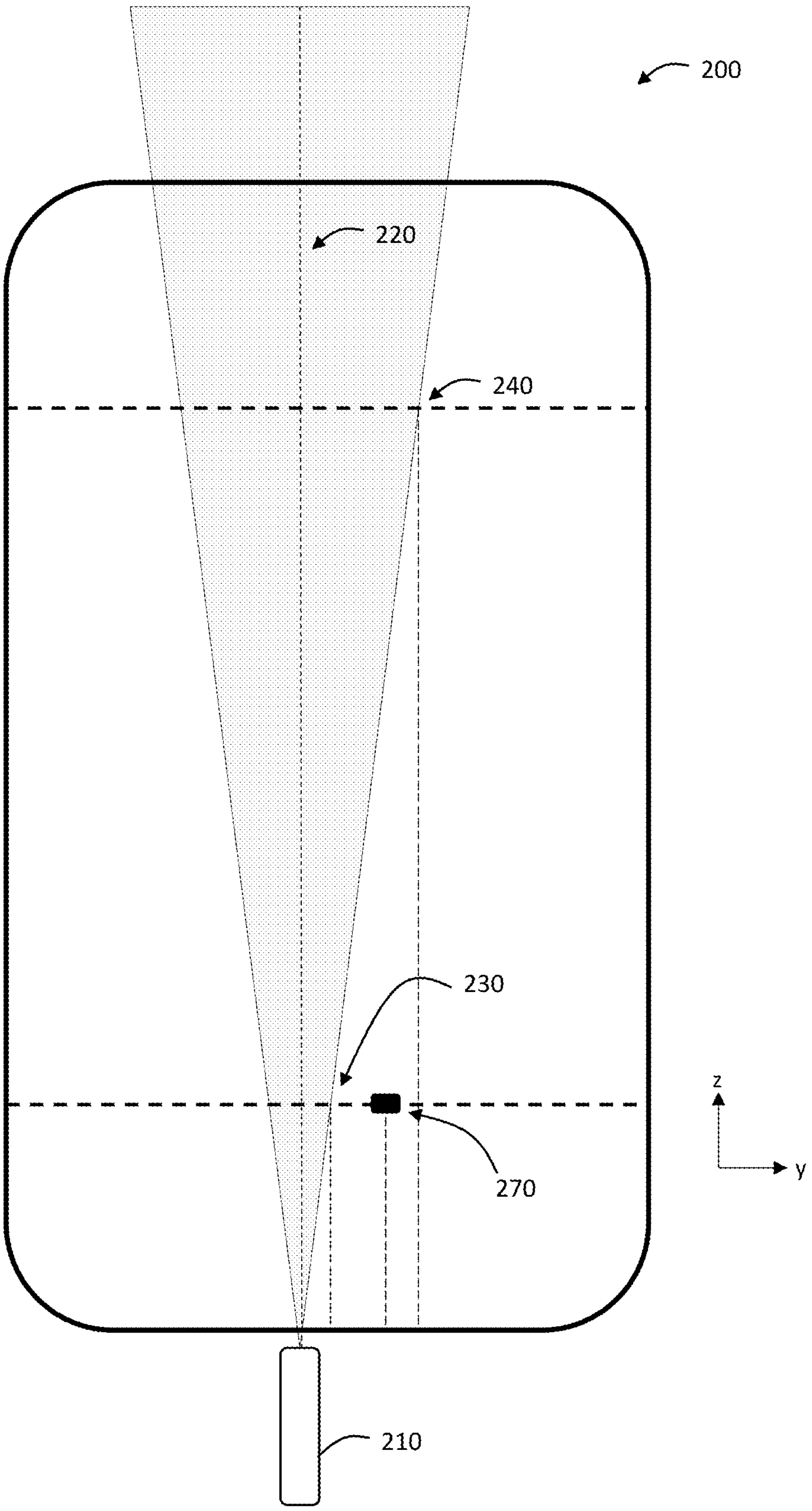
Figure 2C:
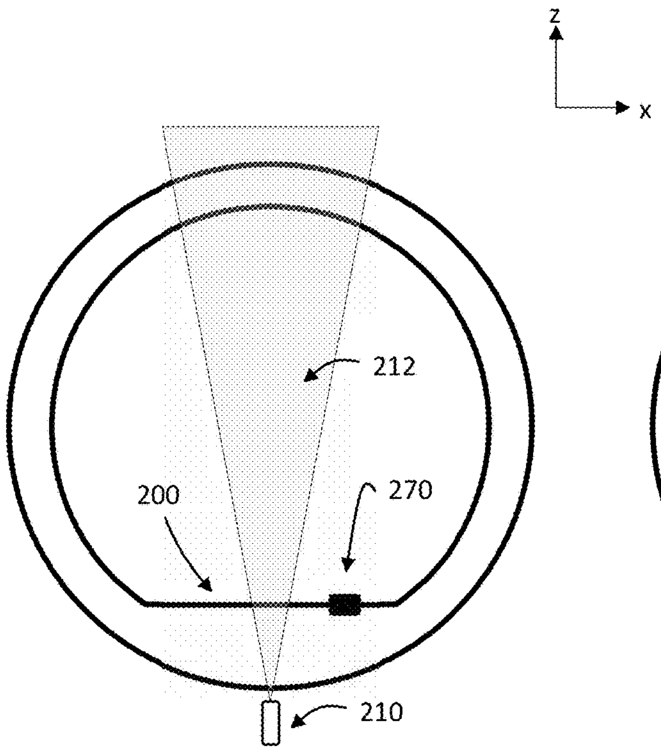
FIGS. 2C-2D depict a front view of an illustrative variation of a radiotherapy system.
Figure 2D:
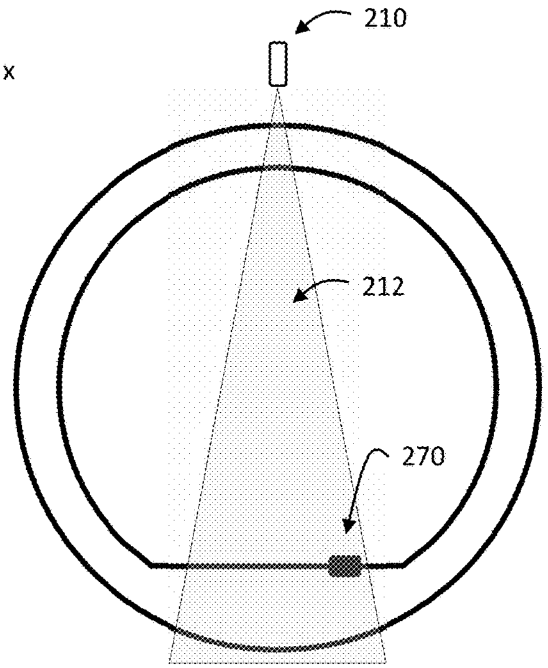

FIGS. 2A-2D schematically depict a variation of a radiotherapy system comprising a therapeutic radiation source and at least one radiation fluence measurement device coupled to the housing of the radiotherapy system. FIGS. 2A-2B depict cross-sectional side views of a radiotherapy system (200) comprising a therapeutic radiation source (210) at a top position (i.e., a firing angle of 0°) and at a bottom position (i.e., a firing angle of 180°). The radiotherapy system (200) may comprise a system housing that has a surface, and a portion of the housing surface may define a bore. In some variations, the housing surface may comprise a bore tube where the tube walls define the bore wall. The central axis of the therapeutic radiation source (which is, in this example, a linac) is represented by a centerline (220). The centerline (220) may also be the center line of the radiation beam emitted by the linac. The centerline (220) may be determined using a computational model of the therapeutic radiation source. At least one radiation fluence measurement device (270) may be coupled to a housing surface in such a location that it measures exit beams. For example, a radiation fluence measurement device may be coupled to a housing location on the bore wall. As described previously, the linac (210) may be moved around the patient area, and in some variations, may be rotated by a circular or ring gantry about the patient area. The fluence measurement device (270) may be coupled to the housing at a location such that it may acquire measurements of the exit beam with little or interference of the entrance beam. That is, the at least one radiation fluence measurement device may be coupled to a housing surface such that it is outside of the entrance irradiation field and within the exit irradiation field. For example, a fluence measurement device (270) may be located within a range defined by $D_{diff}$, as depicted in FIG. 2A. In some variations, the fluence measurement device (270) may be located at an offset from the centerline (220). The offset distance may be in a range that is determined by the irradiation field sizes of the entrance beam and the exit beam, as explained further below.

FIGS. 2A (side cross-sectional view) and 2D (front view) depict one configuration of the radiotherapy system where the linac (210) is located at the top position (i.e., 0°) and the MV detector (not shown) is located opposite the linac at a bottom position (i.e., 180°). In this configuration, the entrance beam may intersect with the bore wall, and the entrance irradiation field (230) at the intersection of the entrance beam and the bore wall may have a diameter of $d_{entrance}$. The exit beam may intersect with the bore wall furthest from the top position of the linac, and the exit irradiation field (240) at the intersection of the exit beam and the bore wall may have a diameter of $d_{exit}$, which may be larger than $d_{entrance}$. The location of the fluence measurement device (270) is such that it is outside of the edge of the projection of the entrance beam irradiation field on the exit beam irradiation field, but within the exit beam irradiation field. FIGS. 2B (side cross-sectional view) and 2C (front view) depicts another configuration of the radiotherapy system (200) where the linac has moved to a location at the bottom of the gantry (i.e., 180°) and the MV detector (not shown) is located opposite the linac at the top position (i.e., 0°). In this configuration, the fluence measurement device does not interfere with the entrance beam, since it is located outside the edge of the entrance irradiation field. Although the fluence measurement device does not acquire exit beam measurements when the radiotherapy system is in this configuration, the fluence measurement device itself does not affect the radiation beam directed toward the patient area. As long as the fluence measurement device location is outside of the entrance irradiation field it does not interfere with the entrance beam regardless of the position of the linac. A fluence measurement device located within $D_{diff}$ (i.e., outside the entrance irradiation field and inside the exit irradiation field) may be configured to measure the exit beam when the linac is in certain firing positions. The firing positions for which the fluence measurement device can measure the exit beam may be determined experimentally by acquiring MV detector imaging data as the linac rotates through all firing positions and identifying the firing positions for which the fluence measurement device appears in the imaging data. While the fluence measurement device (270) described and depicted in FIGS. 2A-2D is located within the range $D_{diff}$ on the bottom of the bore (i.e., 180°), in other variations, the fluence measurement device may be located at any circumferential location around the bore and within the range $D_{diff}$. For example, the fluence measurement device may be located at the top of the bore (i.e., 0°, on either side of the bore (i.e., 90°, 270°, right and left sides), and/or any other circumferential location (e.g., 30°, 45°, 60°, 75°, 85°, 100°, 120°, 135°, 145°, 150°, 170°, 200°, 205°, 215°, 230°, 250°, 275°, 290°, 300°, 325°, 330°, 345°, 350°, etc.) around the bore. In some variations, a radiotherapy system may comprise a plurality of fluence measurement devices that may be located at multiple circumferential locations around the bore.

The range defined by $D_{diff}$ and depicted in FIGS. 2A-2B specifies the locations where the fluence measurement device can acquire measurements of the exit beam without interfering with the entrance beam. The lower end of the range $D_{diff}$ is the edge of the projection of the entrance beam irradiation field on the exit beam irradiation field, and the upper end of the range $D_{diff}$ is the edge of the exit beam irradiation field. The range $D_{diff}$ may vary according to the configuration(s) of the beam-shaping assembly. For example, $D_{diff}$ may vary depending on the size of the aperture(s) of the jaws and/or collimators of the beam-shaping assembly. The range $D_{diff}$ may be determined by analytical calculations, for example, calculations based on the source-to-axis distance, the source-to-bore tube distance, and/or the irradiation field size, dose calculations, and/or Monte Carlo simulations. Alternatively, or additionally, the range $D_{diff}$ may be measured by placing radiographic film (or any fluence measurement device) at the bore wall closest to the linac, activating the therapeutic radiation source, measuring the size of the radiation pattern on the film, and repeating the same steps but instead placing the film at the bore wall furthest from the linac. The distance $D_{diff}$ may be calculated by taking the difference between the radius of the exit irradiation field and the radius of the entrance irradiation field, that is:

$$D_{diff} = r_{exit} - r_{entrance} = \frac{d_{exit}}{2} - \frac{d_{entrance}}{2}$$

These measurements may be repeated if there are changes in the configuration of the beam-shaping assembly. Changing the configuration of the beam-shaping assembly may change the field size of the entrance irradiation field and the exit irradiation field, which may then change the value of $D_{diff}$, and/or shift the location of the range $D_{diff}$. In some variations, the location(s) of the one or more fluence measurement devices may be adjusted when the configuration of the beam-shaping assembly changes.

The location of the one or more fluence measurement devices may be defined relative to the centerline (220) of the linac. In some radiotherapy systems, the MV detector may be positioned such that it is centered to the centerline (220) of the linac. In contrast, the fluence measurement devices described herein are instead positioned at an offset, i.e., $D_{offset}$, from the centerline of the linac. In some variations, the offset from the centerline (220) may be derived from the entrance irradiation field and exit irradiation field as follows:

$$D_{offset} = r_{entrance} + k, \text{ where } 0 \le k \le D_{diff}$$

where $r_{entrance}$ is the radius of the entrance irradiation field $$\left(\text{i.e., } r_{entrance} = \frac{d_{entrance}}{2}\right),$$

and k is any value between zero and $D_{diff}$, where $D_{diff}=r_{exit}-r_{entrance}$. In some variations, k may be selected by a user, and/or may be set at a default value during machine installation and/or treatment planning. For example, k may be selected to be $$\frac{D_{diff}}{2},$$

which allows a radiation fluence measurement device to measure radiation in the middle range of $D_{diff}$. In some variations, the offset $D_{offset}$ from the centerline may be at least about 0.4 cm, at least about 0.5 cm, at least about 0.7 cm, or at least about 0.8 cm. In some variations, the offset distance $D_{offset}$ may be greater than or equal to half a radiation field size (e.g., the size of the exit irradiation field) at the housing surface. Alternatively, in some variations, a fluence measurement device may be located at an offset from the centerline (220) that is outside of the exit irradiation field, i.e., outside of the range $D_{diff}$. Fluence measurement devices positioned outside of the therapeutic radiation source beam (e.g., outside the entrance irradiation field and/or outside the exit irradiation field) may be used to measure ambient radiation and may, for example, facilitate the detection of whether scattered radiation exceeds a safety threshold.

A radiotherapy system may comprise at least one radiation fluence measurement device that is configured to be positioned and/or moved independently of the position and/or motion of a therapeutic radiation source. In some variations, a position of at least one radiation fluence measurement device may be independent of a position of at least one therapeutic radiation source. In some variations, a motion of at least one radiation fluence measurement device may be independent of a motion of at least one therapeutic radiation source. In some variations, a position and/or motion of a radiation fluence measurement device may be controlled by a first motion system. In some variations, a position and/or motion of a therapeutic radiation source may be controlled by a second motion system. In some variations, the first motion system may be configured to operate synchronously with the second motion system. In some variations, the first motion system may be configured to operate asynchronously or otherwise independently of the second motion system. For example, a radiation fluence measurement device may be stationary while a therapeutic radiation source rotates. In some variations, a therapeutic radiation source may spin at a rate of, for example, at least 0.5 RPM, at least 60 RPM, or any other suitable rotational rate.

Figure 2E:
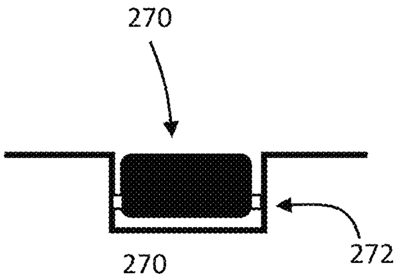
FIGS. 2E-2I depict cross-sectional views of illustrative variations of mounting a radiation fluence measurement device on a radiotherapy system.
Figure 2F:
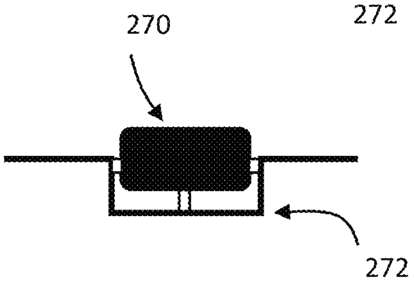
Figure 2G:
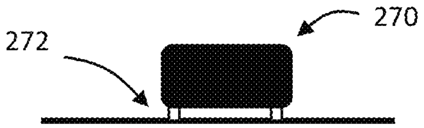

In some variations, a radiation fluence measurement device may be coupled to the surface of the system housing using a stationary mount. FIGS. 2E-2G depict variations of a stationary mount that may be used to couple a radiation fluence measurement device to a system housing or cover. A radiation fluence measurement device (270) may be coupled to the system housing using any suitable attachment mechanism, for example, one or more pins, screws, tape, hook and loop fasteners, or any other attachment mechanism (272) that is configured to temporarily, or permanently, couple the radiation fluence measurement device to the housing surface. In some variations, pins, screws, tape, hook and loop fasteners, wheels or tracks, movable mount(s), or any other attachment mechanism, alone or in combination, may be used to temporarily, or permanently, couple a fluence measurement device to the housing surface. In some variations, a radiation fluence measurement device may be coupled to the surface of the housing such that it is flush with the housing surface, as shown in FIG. 2E. In other variations, a radiation fluence measurement device may be coupled to the housing surface such that at least a section of the radiation fluence measurement device protrudes from the mounting surface and at least a section of the radiation fluence measurement device is obscured by the mounting surface. For example, FIG. 2F depicts an example where the fluence measurement at least partially protrudes from the housing surface. FIG. 2G depicts an example where the fluence measurement device entirely protrudes from the housing surface. A housing surface may comprise one or more grooves or recesses within which the radiation fluence measurement device may be coupled. In some variations, the radiation fluence measurement device may protrude from said grooves or recesses. In some variations, a radiation fluence measurement device may be coupled to the housing surface such that a radiation fluence measurement device does not protrude from the grooves or recesses.

Figure 2H:
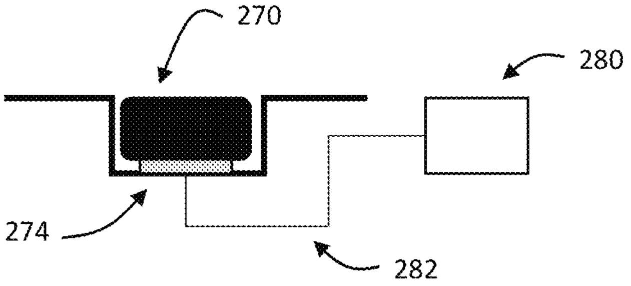
Figure 2I:
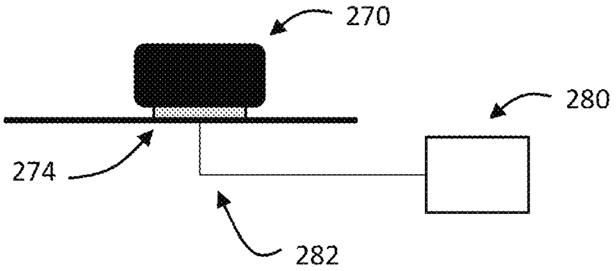

In some variations, a radiation fluence measurement device may be coupled to the surface of the system housing using a movable mount. As examples, FIGS. 2H-2I depict variations of movable mount mechanisms that may be used to couple a radiation fluence measurement device to the housing surface. In some variations, a movable mount may be configured to move along a surface via, for example, wheels or tracks. In some variations, the radiation fluence measurement device may be laterally movable along the housing surface (e.g., along the X-axis) and/or longitudinally movable along the housing surface (e.g., along the Y-axis). A fluence measurement device that is movable along the Y-axis (e.g., IEC-Y) may be able to measure radiation changes along the Y-axis for evaluating Y-axis symmetry. Similarly, a fluence measurement device that is movable along the X-axis (e.g., IEC-X) may be able to measure radiation changes along the X-axis for evaluating X-axis symmetry. In some variations, the radiation fluence measurement device may be coupled to a movable mount but remain in a fixed location along the housing surface. In some variations, the radiation fluence measurement device may be coupled to a surface of the housing at a location determined by a radiotherapy treatment plan fluence map.

Alternatively, or additionally, a movable mount may be connected to an actuator (274). The actuator (274) may comprise one or more of a piezo actuator, linear motor, voice coil, and/or any other suitable motor. In some variations, the actuator may be connected via wires (282) to and controlled by a controller (280). The controller (280) may be in communication with the radiotherapy system controller (110). In some variations, the controller may send commands to the actuator to move a movable mount from a first position to a second position. In some variations, the controller may operate in a closed-loop system, where the location of the fluence measurement device may be automatically adjusted based on the parameters of the treatment plan. In some variations of a closed-loop system, a controller may control an actuator without user input. In some variations, a controller may receive feedback in the form of data from the radiotherapy system and/or radiotherapy treatment plan, and send commands to the actuator in a near-real time response to said data. The radiotherapy system data may comprise one or more of a patient platform location and/or motion, and beam shaping assembly location and/or motion. In some variations, the data of a beam shaping assembly may comprise data on the width of the open jaws and/or multi-leaf collimator (MLC) configuration. In some variations, the commands from the controller may comprise a change in position and/or motion of the movable mount based on the width of the open jaws and/or MLC configuration. The motion and/or position of a radiation fluence measurement device coupled to a movable mount may be adjusted by the controller in response to the open jaw width. The width of the open jaws may impact the width of the emitted radiation field, which may change the values of $D_{offset}$ and/or $D_{diff}$. In some variations, the location of a radiation fluence measurement device may be selected to limit or reduce casting of a shadow on the MV detector. The location of a radiation fluence measurement device may optionally be adjusted according to a patient's physical geometry and/or size and/or the beam collimation configuration. In some variations, the controller of a closed-loop system may send commands to adjust the location and/or motion of at least one radiation fluence measurement device to measure the exit beam without interfering with the entrance beam. Automatically moving the fluence measurement device depending on the location of the therapeutic beam may help the fluence measurement device measure the exit beam without interfering with the entrance beam. For example, the fluence measurement device may be moved to a location that is outside of the range defined by $D_{diff}$ (e.g., outside of $d_{exit}$) when the linac is on the same side as the fluence measurement device and then moved to a location between the linac centerline (220) and the edge of the entrance irradiation field when the linac is on the opposite side as the fluence measurement device. As an illustration, when the linac is moved to the top gantry location (e.g., firing position 0°) and the fluence measurement device is located along the bottom of the gantry (e.g., close to firing position 180°), the fluence measurement device may be moved to a location between the linac centerline (220) and the edge of the entrance irradiation field, i.e., as defined by $d_{entrance}$. When the linac is moved to the bottom gantry location (e.g., firing position 180°), the fluence measurement device may be moved to be at any location outside of the range $D_{diff}$. The location of the fluence measurement device may be adjusted based on the MLC configuration and depending on the leaf openings, the fluence measurement device may be moved to other locations such that the exit beam (also referred to as exit radiation) may be measured without interfering with the entrance beam (also referred to as entrance radiation). For example, the treatment plan may include MLC configurations (e.g., patterns of MLC leaf openings) and/or jaw opening(s) that result in an entrance beam having an entrance irradiation field size. Based on the MLC and/or jaw configurations, the controller of a closed-loop system may send commands to the actuator to move the fluence measurement device to a location that does not interfere with the entrance beam and may store the location of the fluence measurement device in its processor memory.

In some variations, at least one radiation fluence measurement device may be movable independently of at least one therapeutic radiation source. The radiation fluence measurement device may be moved by commands sent to it by a controller, e.g., controller (280) or system controller (110). In some variations, the controller may control the position and motion of a radiation fluence measurement device in an open loop system. In some variations of an open loop system, a controller may control an actuator in response to a manual user input. For example, a user may input a target position for at least one radiation fluence measurement device and a controller may move the radiation fluence measurement device to the target position. In some variations, the controller may respond to a combination of user inputs and data received from the actuator or system. For example, a user may manually adjust the location and/or motion of at least one radiation fluence measurement device based on data received from the beam shaping assembly. In some variations, a user may input commands to control the location and/or motion of one or more of a therapeutic radiation source, a patient platform, and a radiation fluence measurement device.

In the example radiotherapy system of FIGS. 2A-2D, the radiation fluence measurement device is coupled to the surface of the housing, however, in other variations, the radiation fluence measurement device may be coupled beneath the housing surface such that when the housing is assembled over the gantry, the fluence measurement device is enclosed within the housing. A radiation fluence measurement device coupled beneath the housing surface may also be movable using one or more of the mechanisms described above. Alternatively, or additionally, in radiotherapy systems that have a rotatable gantry comprising a rotatory component (e.g., drum or disc) that is coupled to a stationary frame, a fluence measurement device may be coupled to the stationary frame using any of the attachment mechanisms and/or movable mounts described herein. The location of the fluence measurement device may be selected based upon the same factors described herein and conceptually depicted in FIGS. 2A-2D.

In some variations, a radiation fluence measurement device may be coupled to any radiotherapy system component that does not move in synchronicity with the therapeutic radiation source. For example, a radiation fluence measurement device may be coupled to a movable arm in communication with a controller that is configured to adjust the location of the fluence measurement device by adjusting the position of the arm. The movable arm may have a stowed configuration where the fluence measurement device is not at a location where it can make fluence measurements from the therapeutic radiation source and a deployed configuration where the fluence measurement device is at a location where it can measure the radiation fluence of one or more of the entrance beam and/or exit beam. In the stowed configuration, the movable arm and the fluence measurement device may be outside of the motion path of the therapeutic radiation source. In some variations, this movable arm may be located below the plane of the patient platform (e.g., underneath the patient platform). The location of the fluence measurement device when the movable arm is in the deployed configuration may be any of the locations described herein, for example, at a location such that it may measure the exit beam without interfering with the entrance beam. A fluence measurement device coupled to a movable arm may be included in radiotherapy systems comprising a bore (e.g., the movable arm may be located within the system housing covers) as well as in radiotherapy systems that do not have a bore, such as systems where the therapeutic radiation source is mounted on a C-arm or a robotic arm. Alternatively, or additionally, a fluence measurement device may be coupled to the patient platform. In some variations, a fluence measurement device coupled to a movable arm may also be movable along a longitudinal axis (e.g., Y-axis, IEC-Y) and/or a lateral axis (e.g., X-axis, IEC-X) using any of the motion mechanisms described herein.

A radiotherapy system may comprise a plurality of radiation fluence measurement devices that are coupled to (e.g., integrated, embedded, etc.) to the system housing or covers, e.g., the bore. The plurality of radiation fluence measurement devices may be located such that they can sample the exit beam without interfering with the entrance beam, as described above with regard to FIGS. 2A-2E. FIGS. 3A-3E depicts variations of a radiotherapy system comprising a therapeutic radiation source and a plurality (i.e., one or more) of radiation fluence measurement devices coupled to a housing surface. A radiotherapy system may comprise a first radiation fluence measurement device and a second radiation fluence measurement device. They may each be coupled to the system housing at locations that are outside of the entrance irradiation field but inside of the exit irradiation field. For example, the first and second fluence measurement devices may each be at locations at an offset from the linac centerline and/or as specified by $D_{diff}$, as explained above with regard to FIGS. 2A-2D. In some variations, the first radiation fluence measurement device may be a different type of radiation fluence measurement device than the second radiation fluence measurement device. For example, the first radiation fluence measurement device may be an ion chamber and the second radiation fluence measurement device may be a diode or an array of radiation detectors. In some variations, the first and second radiation fluence measurement devices may be the same type of device. For example, the first and second radiation fluence measurement devices may both be ion chambers.

Figure 3A:
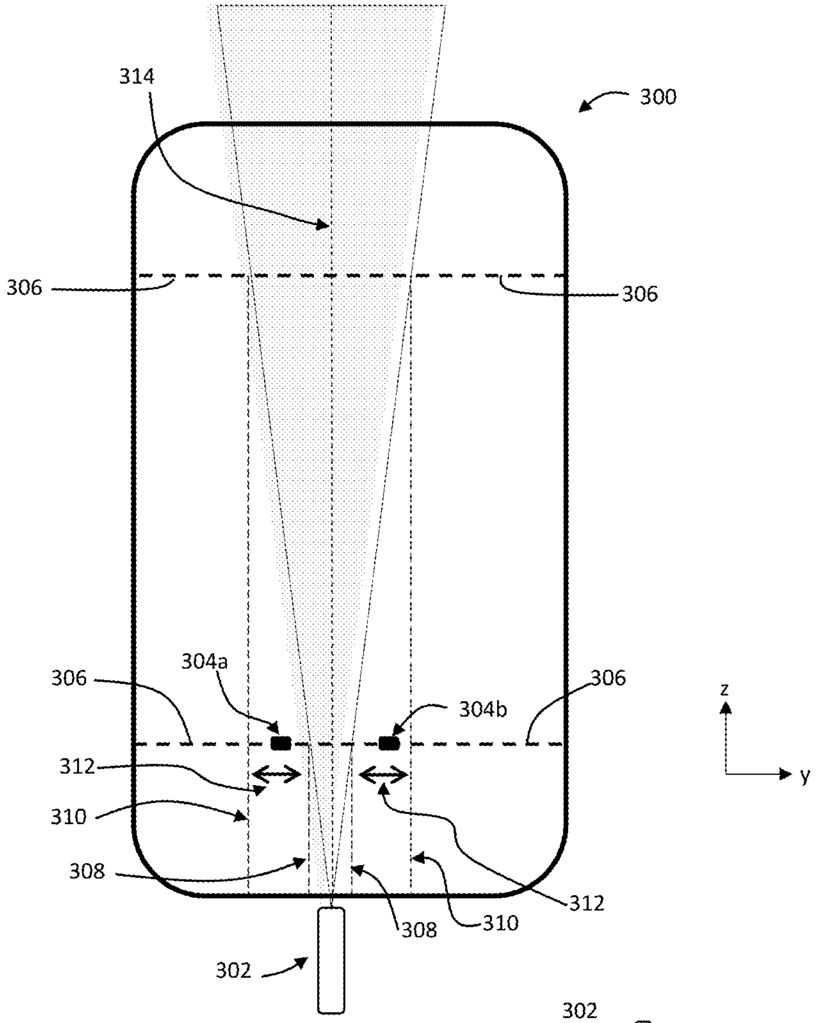
FIG. 3A depicts a front cross-sectional view of an illustrative variation of a radiotherapy system.
Figure 3B:
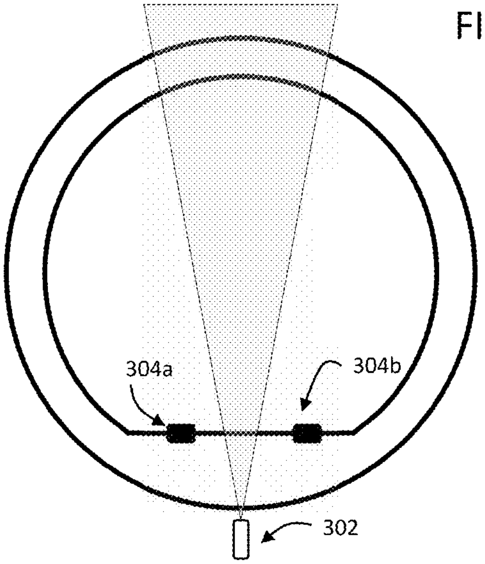
FIGS. 3B and 3C depict a front view of an illustrative variation of a radiotherapy system.
Figure 3C:
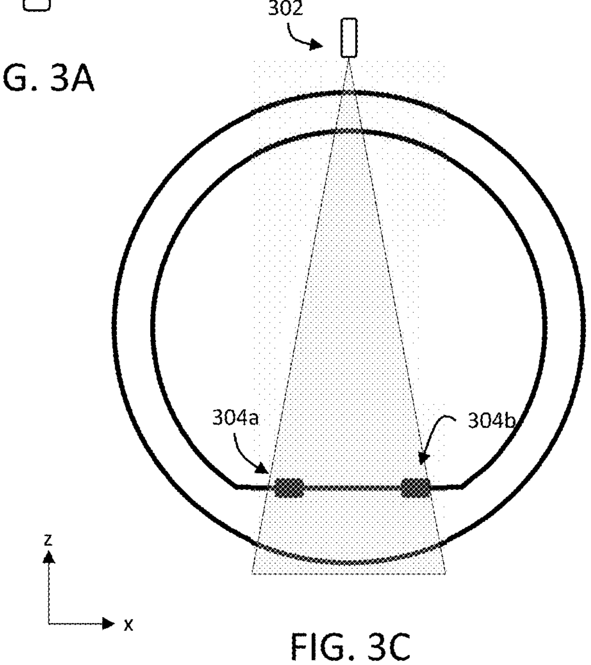

In some variations, the second radiation fluence measurement device may be coupled to the housing surface in a different lateral position (along the Y-axis) than the first radiation fluence measurement device. FIG. 3A depicts a schematic cross-sectional side view of a radiotherapy system (300) comprising a therapeutic radiation source (302) that is configured to emit radiation along the Z-axis. One or more radiation fluence measurement devices (304) may be coupled to the housing along the bore wall (306), where the first fluence measurement device (304*a*) may be located at a first location along the Y-axis and the second fluence measurement device (304*b*) may be located at a second location along the Y-axis. In some variations, a second radiation fluence measurement device may be axially adjacent on a Y-axis to a first radiation fluence measurement device; that is, at the same circumferential location on the bore (e.g., 180° as depicted in FIG. 3A), but at different locations along the Y-axis. Both fluence measurement devices may be at a location that is outside of the entrance beam irradiation field and within the exit beam irradiation field, e.g., within the range $D_{diff}$ around the beam, as described above and delineated by dotted lines (308, 310) in FIG. 3A). In some variations, the first and second fluence measurement devices may be movable within the range $D_{diff}$, as represented by arrows (312), using any of the motion mechanisms described herein. Alternatively, or additionally, one or more of the fluence measurement devices may be at a fixed or stationary location along the system housing. As depicted in FIG. 3B, when the therapeutic radiation source (302) is at the bottom gantry location (i.e., firing position 180°), the first and second fluence measurement devices (304*a*, 304*b*) are both outside of the entrance irradiation field. When the therapeutic radiation source (302) is moved to the top gantry location (i.e., firing position 0°) as depicted in FIG. 3C, the first and second fluence measurement devices (304*a*, 304*b*) are both within the exit irradiation field, and are configured to measure the radiation exiting the patient area within the bore. A radiotherapy system comprising additional fluence measurement devices at multiple locations within the exit irradiation field may provide additional data about the radiation emitted to the patient area for quality assurance checks and/or dose calculations.

In some variations, the offset distance of each radiation fluence measurement device relative to the centerline (314) may be substantially equal. In some variations, a substantially equal position of multiple radiation fluence measurement devices relative to a therapeutic radiation source centerline may occur when the multiple radiation fluence measurement devices are positioned equidistant from the centerline while accounting for the tolerance of the positioning mechanism. In some variations, the offset distance of each radiation fluence measurement device relative to the centerline of a therapeutic radiation source may be substantially different, i.e., when the multiple radiation fluence measurement devices are positioned non-equidistantly from the centerline while accounting for the tolerance of the positioning mechanism.

Figure 3D:
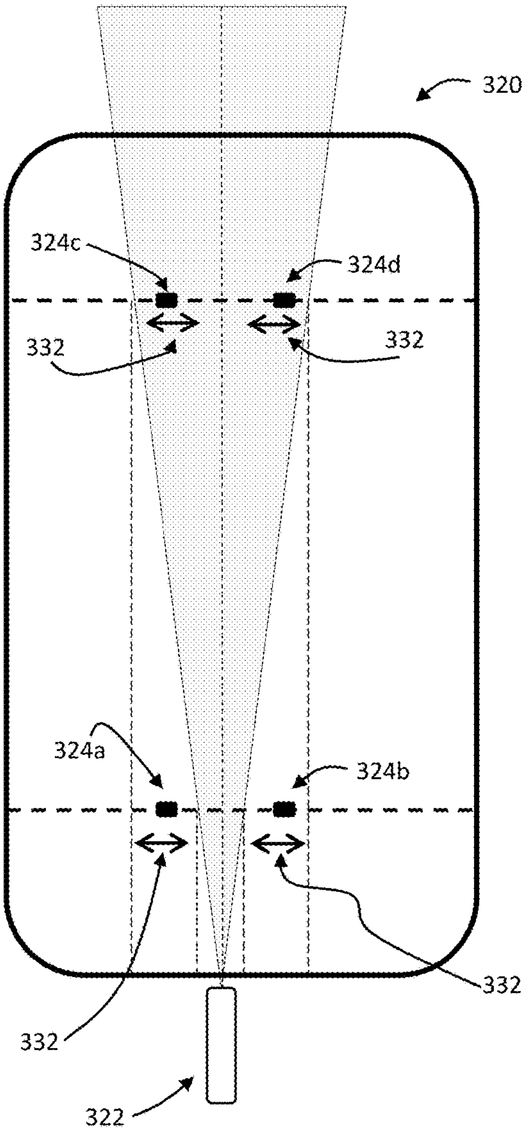
FIGS. 3D and 3E depict side cross-sectional views of an illustrative variation of a radiotherapy system.
Figure 3E:
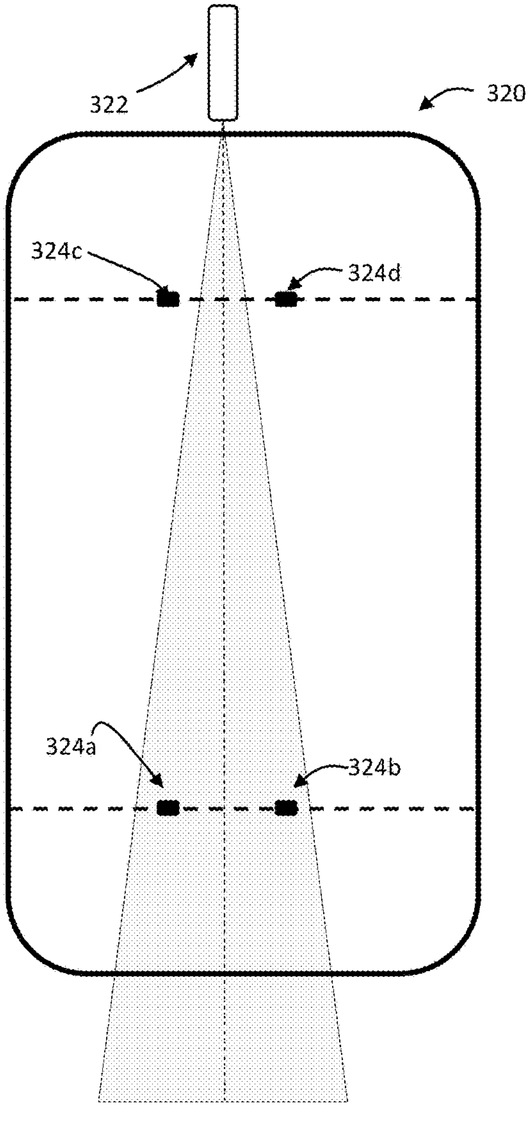

Alternatively, or additionally, the second fluence measurement device may be at a different circumferential location on the bore from the first fluence measurement device (e.g., the first fluence measurement device may be at 180° while the second fluence measurement device is at 90° or 0°). The first and second fluence measurement devices may be at the same location along the Y-axis (and at different circumferential locations) or at different locations along the Y-axis. FIGS. 3D and 3E depict variations of a radiotherapy system (320) comprising a therapeutic radiation source (322) and a plurality of fluence measurement devices (324*a*, 324*b*, 324*c*, 324*d*) that are coupled to the system housing within the bore. While four fluence measurement devices are depicted in FIGS. 3D-3E, it should be understood that in some variations there may be fewer than four fluence measurement devices or more than four fluence measurement devices. The first and second fluence measurement devices (324*a*, 342*b*) may be located similarly to those described in FIGS. 3A-3C (i.e., at the bottom of the bore, at an angle 180°), and the third and fourth fluence measurement devices (324*c*, 324*d*) may be located opposite the first and second fluence measurement devices (i.e., at the top of the bore, at an angle 0°). The second and fourth fluence measurement devices (324*b*, 324*d*) may be at the same or different location along the Y-axis, and/or the first and third fluence measurement devices (324*a*, 324*c*) may be at the same or different location along the Y-axis. One or more of the fluence measurement devices (324*a*, 324*b*, 324*c*, 324*d*) may be movable along the Y-axis in the direction of the arrows (332) using any of the motion mechanisms described herein. Alternatively, or additionally, one or more of the fluence measurement devices may be at a fixed or stationary location along the system housing. The locations of one or more of the fluence measurement devices (324*a*, 324*b*, 324*c*, 324*d*) may be within the range $D_{diff}$ as described previously, or may be outside of the range $D_{diff}$.

FIG. 3D depicts the configuration of the radiotherapy system (320) when the therapeutic radiation source is at the bottom of the bore (i.e., angle 180°). In this configuration, the first and second fluence measurement devices (324*a*, 324*b*) are not within the entrance irradiation field, but the third and fourth fluence measurement devices (324*c*, 324*d*) are within the exit irradiation field. FIG. 3E depicts the configuration of the radiotherapy system (320) when the therapeutic radiation source is at the top of the bore (i.e., angle 0°). In this configuration, the third and fourth fluence measurement devices (324*c*, 324*d*) are not within the entrance irradiation field, but the first and second fluence measurement devices (324*a*, 324*b*) are within the exit irradiation field. With the additional fluence measurement devices, the radiotherapy system (320) is configured to measure the exit beam when the therapeutic radiation source (322) is located at the bottom of the bore and when it is located at the top of the bore. In contrast, the radiotherapy system (300) may be configured to measure the exit beam when the therapeutic radiation source (302) is located at the top of the bore, but not when the therapeutic radiation source is located at the bottom of the bore. The additional fluence measurement devices may facilitate the measurement of the exit beam at more circumferential locations about the gantry, and may provide information about the exit beam and/or delivered dose as the therapeutic radiation source rotates about the patient area. Alternatively, or additionally, a radiotherapy system may comprise one or more fluence measurement devices at the left and right sides of the bore, e.g., circumferential locations at 90° and 270°. For example, a radiotherapy system may comprise a first fluence measurement device at 0°, a second fluence measurement device at 90°, a third fluence measurement device at 180°, and a fourth fluence measurement device at 270°. This configuration may facilitate the acquisition of four fluence measurements per rotation of the therapeutic radiation source on the gantry. As with the other variations described herein, one or more of the fluence measurement devices may be coupled to the system housing at locations that are outside the entrance irradiation field but within the exit irradiation field. Alternatively, or additionally, one or more of the fluence measurement devices may be coupled to the system housing at locations that are outside the exit irradiation field.

Radiopaque Fiducials

Some variations of a radiotherapy system may optionally comprise one or more fiducials coupled to a system housing. The fiducials may be radiopaque and comprise one or more materials that absorb or block radiation such that the fiducials are detectable by a radiation detector. That is, radiopaque fiducials may comprise materials such that they cast a "shadow" on the MV detector. Example of materials may include, but are not limited to, tungsten, titanium, gold, iron, and metallic alloys such as a nickel-titanium alloy. In some variations, the fiducials may comprise radiation-emitting materials. The intensity and/or quantity of radiation emitted by a fiducial may be lower than the intensity and/or quantity of radiation emitted by the therapeutic radiation source. In some variations, a collimating element may be included with the radiation-emitting fiducials. An example of a collimating element may comprise shielding material with a small bore within which the radiation-emitting fiducial is located. In some variations, the axis of the bore of the shielding material may be tilted away from the patient area and optionally tilted toward the fluence measurement device and/or MV detector. The lowered radiation level emitted by the fiducials may reduce the radiation exposure to the patient and/or personnel, and may also help distinguish the radiation emitted by the fiducial from the radiation emitted by the therapeutic radiation source. Radiation-emitting fiducials may comprise one or more X-ray emitting radionuclides such as 137-Cs, 241-Am, Co-60, etc. In some variations, radiation-emitting fiducials may comprise positron-emitting radionuclides such as Na-22, 64-Cu. The radiation from the radiation-emitting fiducials may be detected by the MV detector and/or CT detector and/or PET detectors of a radiotherapy system. The examples described below depict systems comprising radiopaque fiducials, however, it should be understood that the same system features and structures may apply to radiotherapy systems with radiation-emitting fiducials. In some variations, a radiotherapy system may comprise a combination of radiopaque and radiation-emitting fiducials. In some variations, a similar same effect may be achieved by engraving cavities in the bore tube.

Optionally, some variations of a radiotherapy system may comprise at least one fiducial that may facilitate the evaluation of the position and/or orientation of components of the radiotherapy system. For example, radiopaque fiducials coupled to the surface of the bore tube and the location of the fiducials as reflected in the MV detector imaging data may help determine whether the bore tube and the therapeutic radiation source and/or the MV detector are installed correctly relative to each other. Changes in the location of the fiducials as determined by the acquired MV detector data may also indicate that the bore tube and/or therapeutic radiation source and/or MV detector have moved. Changes in the location of the fiducials may also indicate a change in the relative orientation of the bore tube, therapeutic radiation source, and/or MV detector. Location changes of the fiducial(s) that are greater than an acceptable threshold or outside an acceptable range may trigger the radiotherapy system to generate a notification. The notification may include a graphical message output to a display and/or an audible sound output to a speaker that alerts the operator to check the position of the bore tube (and/or system housing), therapeutic radiation source, and/or MV detector. For example, if the rotating gantry deflects or tilts from its intended rotational axis, the positions of the therapeutic radiation source and MV detector relative to the radiopaque fiducials (which may be fixedly coupled to the stationary bore tube) may change, and this change may trigger the generation of a notification. During installation of the radiotherapy system, radiopaque fiducials coupled to the system housing may help the installation personnel determine whether the housing covers (e.g., bore tube) are properly positioned over the gantry and that it is aligned according to specification. In some variations, a radiotherapy system may comprise a radiation fluence measurement device and one or more radiopaque fiducials near the radiation fluence measurement device. For example, a radiopaque fiducial may be located at the same Y-axis location, but a different circumferential location, as the fluence measurement device.

The one or more fiducials may be fixedly coupled to the housing surface of the radiotherapy system. For example, the radiopaque fiducials may be embedded in the housing surface. In some variations, one or more fiducials may be coupled to the bore wall such that the fiducials are outside the entrance irradiation field (i.e., does not interfere with the entrance beam) but are within the exit irradiation field. For example, the fiducials may be within the range defined by $D_{diff}$, as described and depicted above. In some variations, at least one radiopaque fiducial may be mounted to the housing surface on a stationary mount. In some variations, at least one radiopaque fiducial may be mounted to the housing surface on a movable mount, such as any of the movable mounts described above. The one or more fiducials may facilitate verification of the relative positioning of the radiation fluence measurement device in the irradiation field and/or of the positioning of the bore tube with respect to the other components of the radiotherapy system. In some variations, the position of a given component may be determined by a shadow cast by the component onto the MV detector. In some variations, each of the plurality of radiopaque fiducials may be uniquely identifiable from the other radiopaque fiducials. For example, fiducials may be uniquely identifiable by their shape, size, and/or orientation. In some variations, at least one fiducial may be radiopaque or may have varying degrees of radiopacity. Radiopaque may be rod-shaped, rectangular, spherical, or any other shape. In some variations, the fiducials may have the same shape but have different orientations that vary according to their circumferential location around the bore. For example, a radiotherapy system may comprise a first fiducial at the top (0°) of the bore, a second fiducial on the right (90°) side of the bore, a third fiducial on the bottom of the bore (180°), and a fourth fiducial on the left (270°) side of the bore, and all four fiducials may have an arrow shape. The pointer of the arrow for each of the fiducials may vary for each of the fiducials so that the MV detector image (the "shadow" of the fiducial on the detector) of each fiducial points in a unique direction. For example, the first fiducial may comprise an arrow oriented such that it points out of the bore (along the Y-axis) when imaged on the MV detector, the second fiducial may comprise an arrow oriented such that it points to the right when imaged on the MV detector, the third fiducial may comprise an arrow oriented such that it points to the into the bore when imaged on the MV detector, and the fourth fiducial may comprise an arrow oriented such that it points to the left when imaged on the MV detector.

Figure 4A:
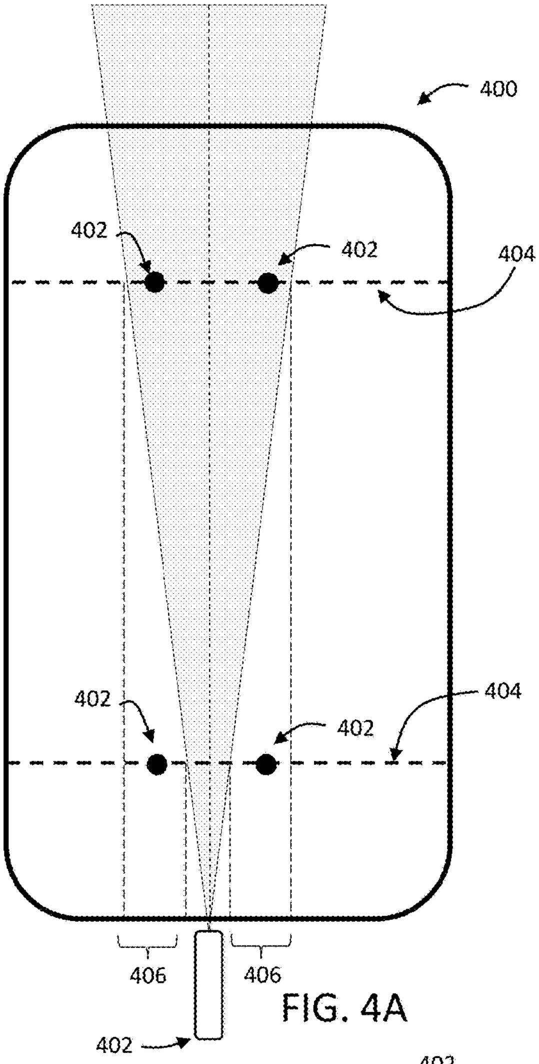
FIG. 4A depicts a side cross-sectional view of an illustrative variation of a radiotherapy system having a radiopaque fiducial.

FIGS. 4A-4E depict variations of radiotherapy systems comprising a therapeutic radiation source and one or more radiation fluence measurement device radiopaque fiducials. Optionally the radiotherapy systems may comprise one or more fluence measurement devices, as described above. The one or more radiopaque fiducials (402) may be coupled to a housing surface of the radiotherapy system. For example, the system housing may comprise a bore tube (404) and the radiopaque fiducials (402) may be coupled to the surface of the bore tube (404). FIG. 4A depicts one variation of a radiotherapy system (400) comprising four radiopaque fiducials (402) along the bore tube (404) surface, where all four of the fiducials are located within the exit irradiation field, but outside the entrance irradiation field, i.e., within the range $D_{diff}$, as described above and represented in the bracketed region (406). Alternatively, or additionally, one or more of the fiducials may be located outside the exit irradiation field.

Figure 4B:
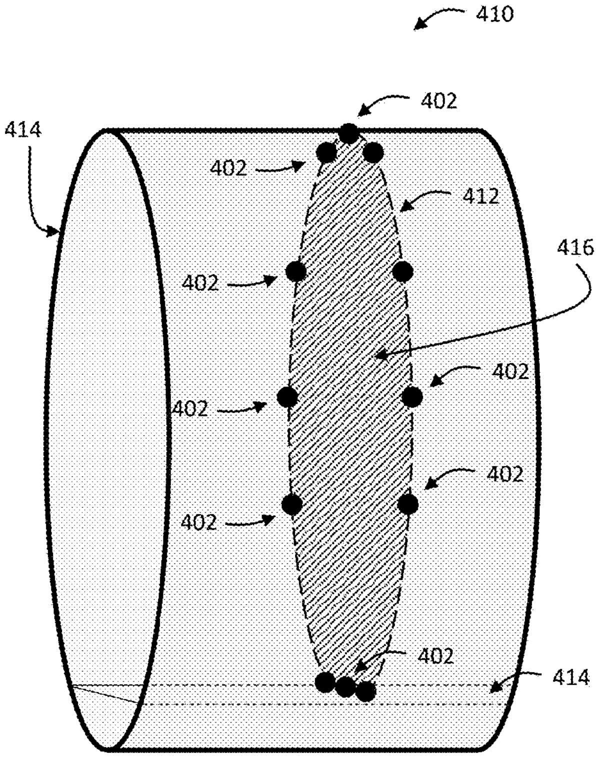
FIG. 4B depicts a perspective view of an illustrative variation of a radiotherapy system having a plurality of radiopaque fiducials.
Figure 4C:
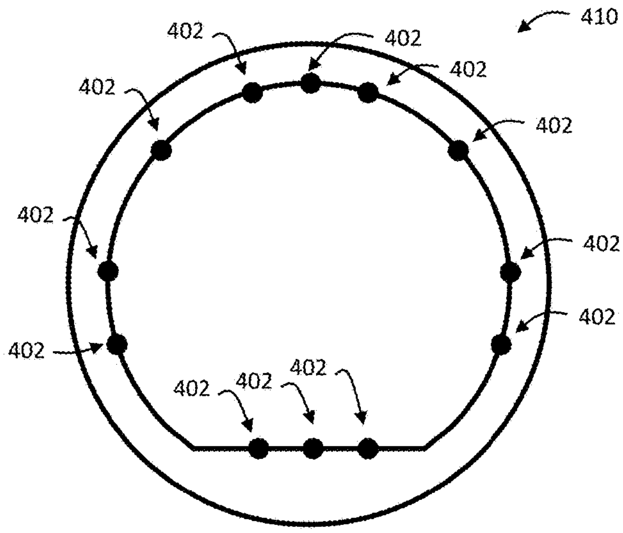
FIG. 4C depicts a front view of an illustrative variation of a radiotherapy system having a plurality of radiopaque fiducials.

In some variations, a plurality of radiopaque fiducials (402) may be distributed around a circumference or perimeter (412) of the bore tube. In some variations, one or more radiopaque fiducials may be distributed around the perimeter of a cross-section of the bore, wherein the cross-section is located a second offset distance from a first position. FIGS. 4B and 4C depict a variation of a radiotherapy system (410) comprising a plurality of radiopaque fiducials (410) coupled along a circumference of the bore wall (414). In some variations, the plurality of radiopaque fiducials may be spaced evenly around the circumference of the bore wall. For example, each fiducial may be located at an angle around the circumference, and the angular interval between fiducials may be the same, e.g., fiducials separated at 45° angular intervals such that there are fiducials located at 0°, 45°, 90°, 135°, 180°, 225°, 270°, and 315° angle locations. Alternatively, or additionally, the angular interval between the fiducials may vary around the circumference of the bore. For example, FIG. 4B depicts an example of a radiotherapy system (410) where some of the fiducials have a constant angular interval for a portion of the bore perimeter or circumference (e.g., along the left and right sides of the bore) and some of the fiducials have a different angular interval for other portions of the bore perimeter or circumference (e.g., along the top and bottom portions of the bore). While the various bores and bore tubes described herein may be depicted as a cylinder with a round cross-section, it should be understood that in some variations, a portion of the bore may have a flat surface. As an example, the bore of the radiotherapy system (410) in FIGS. 4B-4C has a flat portion at the bottom of the bore. One or more radiopaque fiducials (402) and/or fluence measurement devices (not shown) may be coupled to the flattened portion of the bore wall.

Figure 4D:
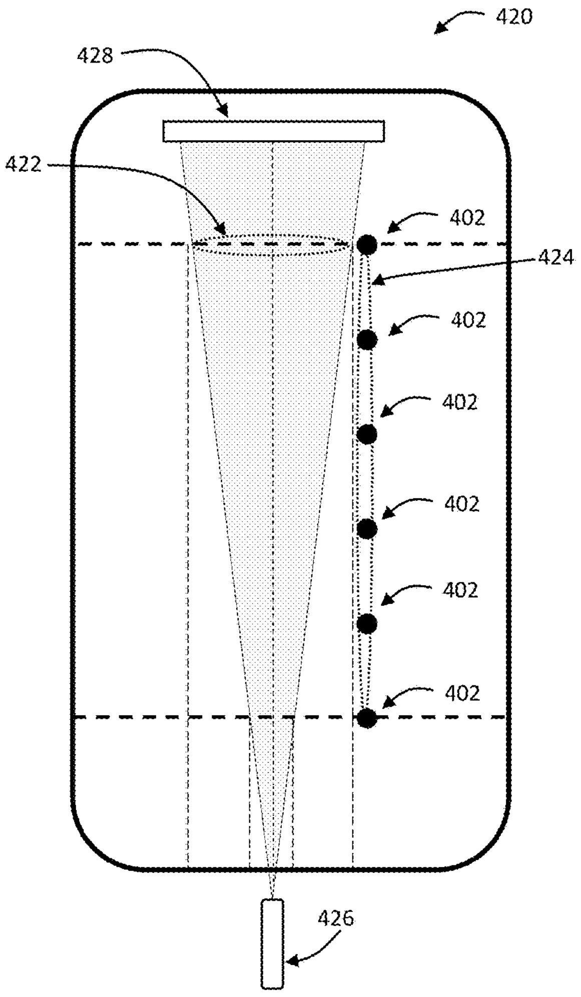
FIG. 4D depicts a side cross-sectional view of an illustrative variation of a radiotherapy system having a plurality of radiopaque fiducials.

In some variations, the fiducials may be arranged around the perimeter (412) of the bore such that they are on a plane (416) that is parallel with a cross section of the bore tube. For example, the plane (416) may be parallel with the cross section of the bore tube taken along the centerline of the therapeutic radiation source. The plane defined by the fiducials may be within the exit irradiation field, on the boundary of the exit irradiation field, or outside the exit irradiation field. FIG. 4D depicts one variation of a radiotherapy system (420) comprising a therapeutic radiation source (426), an MV detector (428), and fiducials (402) that are arranged on a plane (424) that is outside the exit irradiation field (422) of the therapeutic radiation source (426). In this variation, as long as the therapeutic radiation source (426) retains its alignment as it rotates around the bore, the fiducials will not be evident on the MV detector readings. However, if the alignment of the therapeutic radiation source and/or MV detector changes, for example, due to a tilt in the gantry and/or a positional shift of the therapeutic radiation source and/or MV detector, the irradiation field would no longer be parallel with the fiducial plane (424), and one or more of the fiducials (402) may be visible on the MV detector. Alternatively, or additionally, if alignment of the bore tube changes related to the therapeutic radiation source and/or MV detector, one or more of the fiducials (402) may be visible on the MV detector. In this variation, if a shadow of one of more fiducials is apparent on the MV detector, the radiotherapy system may generate a notification comprising a graphical interface and/or audio alerts that indicate a possible need for an alignment check for the bore tube, and/or therapeutic radiation source, and/or MV detector.

Figure 4E:
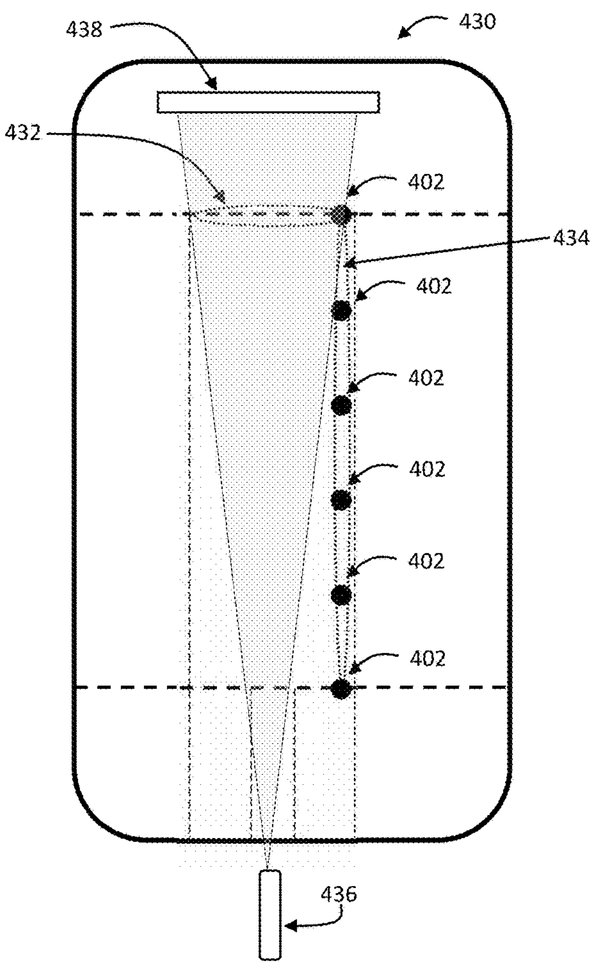
FIG. 4E depicts a cross-sectional view of an illustrative variation of a radiotherapy system having a plurality of radiopaque fiducials.

FIG. 4E depicts another variation of a radiotherapy system (430) comprising fiducials (402) that are arranged on a plane (434) that at least partially overlaps with the exit irradiation field (432) of the therapeutic radiation source. FIG. 4E depicts one variation of a radiotherapy system (430) comprising a therapeutic radiation source (436), an MV detector (438), and fiducials (402) that are arranged on a plane (434) that is outside the exit irradiation field (432) of the therapeutic radiation source (436). In this variation, as long as the therapeutic radiation source (436) retains its alignment as it rotates around the bore, one or more of the fiducials will be evident on the MV detector readings. However, if the alignment of the therapeutic radiation source and/or MV detector changes, for example, due to a tilt in the gantry and/or a positional shift of the therapeutic radiation source and/or MV detector, the irradiation field would no longer be parallel with the fiducial plane (434), and the position of one or more of the fiducials (402) may change and be detected by the MV detector. Alternatively, or additionally, if alignment of the bore tube changes related to the therapeutic radiation source and/or MV detector, the position of one or more of the fiducials (402) may change and be detected by the MV detector. For example, if a shadow of one of more fiducials no longer appears on the MV detector, and/or if the MV detector senses a change in the position of the shadow(s) of one of more fiducials no longer appears on the MV detector, the radiotherapy system may generate a notification comprising a graphical interface and/or audio alerts that indicate a possible need for an alignment check for the bore tube, and/or therapeutic radiation source, and/or MV detector.

While the systems described herein comprise radiation fluence measurement devices and/or fiducials that are located outside of the entrance irradiation field and inside the exit irradiation field, it should be understood that in other variations, the radiation fluence measurement devices and/or fiducials may be located inside the entrance irradiation field or outside the exit radiation field. A radiation fluence measurement device that is located within the entrance beam may affect the radiation directed at the patient area and/or cast a shadow on the MV detector, however, in those radiotherapy systems, the system controller may be configured to account for those artifacts when processing the MV detector data and/or calculating delivered dose. As with the variations described above, the fluence measurement devices and/or fiducials may be coupled to the system housing and may be movable independently of the therapeutic radiation source.

Methods

A radiotherapy system comprising a radiation fluence measurement device coupled to the system housing may be used in various methods to facilitate the measurement of the radiation emitted from the therapeutic radiation source. In one variation, a method may comprise moving the therapeutic radiation source (e.g., using the gantry) to different radiation firing/emission positions about the patient area and acquiring fluence data for each firing position using the fluence measurement device. In another variation, a method may comprise moving the fluence measurement device while the therapeutic radiation source emits radiation from a stationary location. In still another variation, a method may comprise moving both the fluence measurement device and the therapeutic radiation source to known and/or specified locations and acquiring fluence data for each location combination (e.g., a fluence measurement for the therapeutic radiation source at one location and the fluence measurement device at another location). A fluence measurement device coupled to the system housing may facilitate more frequent radiation measurements and/or radiation measurements of different areas of the radiation beam. For example, the radiation fluence data acquired by a fluence measurement device coupled to the system housing may be used to evaluate the beam shape and/or symmetry (e.g., symmetry along the X-axis), confirm MLC and/or jaw collimation patterns, calibrate the MV detector (e.g., calculate a calibration function or mapping between MV detector measurements and fluence measurement device data), and/or detect the cumulative radiation dose delivered in a session of delivery. The radiotherapy system controller may comprise one or more machine-readable memories configured to store radiation measurements from the MV detector and/or fluence measurement device as well as machine-executable instructions for processing the radiation measurements, and one or more processors configured to execute the instructions for analyzing the radiation measurements in accordance with the methods described herein.

Optionally, some radiotherapy systems may comprise one or more fiducials (e.g., radiopaque fiducials) coupled to the system housing. The one or more fiducials may be arranged and configured as described above, and may be combined with any arrangement or number of radiation fluence measurement devices. In some variations, one or more fiducials may be coupled to the bore tube and methods for verifying the position of the bore tube relative to the therapeutic radiation source and/or MV detector may comprise acquiring MV detector image data of the fiducials, determining the position of the fiducials from the acquired and comparing the position with an expected position (e.g., position when the alignment is as desired, such as immediately after installation or calibration) to determine whether the bore tube is tilted and/or displaced from its aligned position. Alternatively, or additionally, the comparison of the measured fiducial position(s) with the expected position(s) may also be used to determine whether the therapeutic radiation source, MV detector, and/or gantry upon which they are mounted are tilted and/or displaced from their aligned position. A radiotherapy system comprising one or more fiducials coupled to the system housing may allow any method where there is an emission of radiation from the therapeutic radiation source to also include regular monitoring of the relative position and/or alignment of the system housing (which may have one or more fluence measurement devices coupled to it) and the gantry-mounted components (e.g., therapeutic radiation source, MV detector, PET detectors, etc.). For example, the alignment and/or position of the system housing and the gantry-mounted components may be monitored during a treatment session with a patient in the patient area by acquiring fiducial position data as the gantry rotates. Confirmation of correct and consistent alignment for the duration of a treatment session may help increase the confidence in the delivered dose calculations. Some variations of QA procedures may comprise monitoring the alignment and/or position of the system housing and the gantry-mounted components as radiation is emitted in the absence of a patient. The emitted radiation may be measured by one or more fluence measurement devices coupled to the housing (as described herein) and/or the MV detector and/or any fluence measurement devices placed in the patient area. Some QA procedures may comprise placing a phantom within the patient area, where the phantom may optionally be anthropomorphic and/or radiation-emitting (e.g., filled with a radioactive fluid, such as a PET-avid fluid). Alternatively, or additionally, a phantom may comprise a portion with varying heights or thickness, for example, a stepped wedge. In some variations, the phantom may comprise one or more fluence measurement devices (e.g., one or more of an ion chamber, a diode array, thin film transistor (TLT), thermoluminescent dosimeter (TLD), film, and/or any radiation photon detection device, etc.). A phantom may have prespecified geometric and material properties. A phantom may optionally comprise one or more of water, plastic, and/or materials having different radiation attenuation properties. For example, a phantom may comprise slabs of plastic and/or compartments filled with water or any other desired fluid. Some phantoms may comprise portions having homogeneous material properties and/or portions with inhomogeneous material properties. Fiducials coupled to the system housing may facilitate the regular and/or constant monitoring of the quality of the generated radiation beam, the relative alignment of the gantry-mounted components and the system housing, and/or the position of the fluence measurement device(s) that are coupled to the system housing.

The methods described herein may be included in QA procedures that take place when there is no patient in the patient area and/or may be performed during a treatment session when radiation is emitted to a patient located in the patient area. While the examples and variations provided below describe moving the therapeutic radiation source while keeping the position of a fluence measurement device fixed or stationary on the system housing, it should be understood that similar methods may comprise moving the fluence measurement device (e.g., along the X-axis) which keeping the therapeutic radiation source fixed or stationary. Alternatively, or additionally, some methods may comprise moving both the fluence measurement device and the therapeutic radiation source in a known (e.g., predetermined) sequence.

One variation of a method for measuring the radiation fluence at different regions of an entrance or exit irradiation field may comprise moving the therapeutic radiation source (e.g., linac) to different firing positions around the patient area, emitting radiation from those firing positions toward the patient area, measuring the emitted radiation for each firing position using a fluence measurement device, and generating a plot that represents the measured radiation at each firing position. For a circular gantry radiotherapy system, the linac may be moved to different firing angles about the patient area. As the linac is moved to, and emitting radiation from, different firing positions, in some variations, the location(s) of the one or more fluence measurement devices may remain fixed (i.e., stationary). Alternatively, or additionally, the location(s) of the one or more fluence measurement devices may be changed as the linac is moved to, and emitting radiation from, different firing positions. For example, the location of a fluence measurement device may be moved to different locations along the X-axis (e.g., IEC-X) for each linac radiation emission. Some methods may comprise placing a phantom and/or patient within the patient area, while other methods may comprise emitting radiation from the linac without a phantom and/or patient within the patient area.

Figure 5:
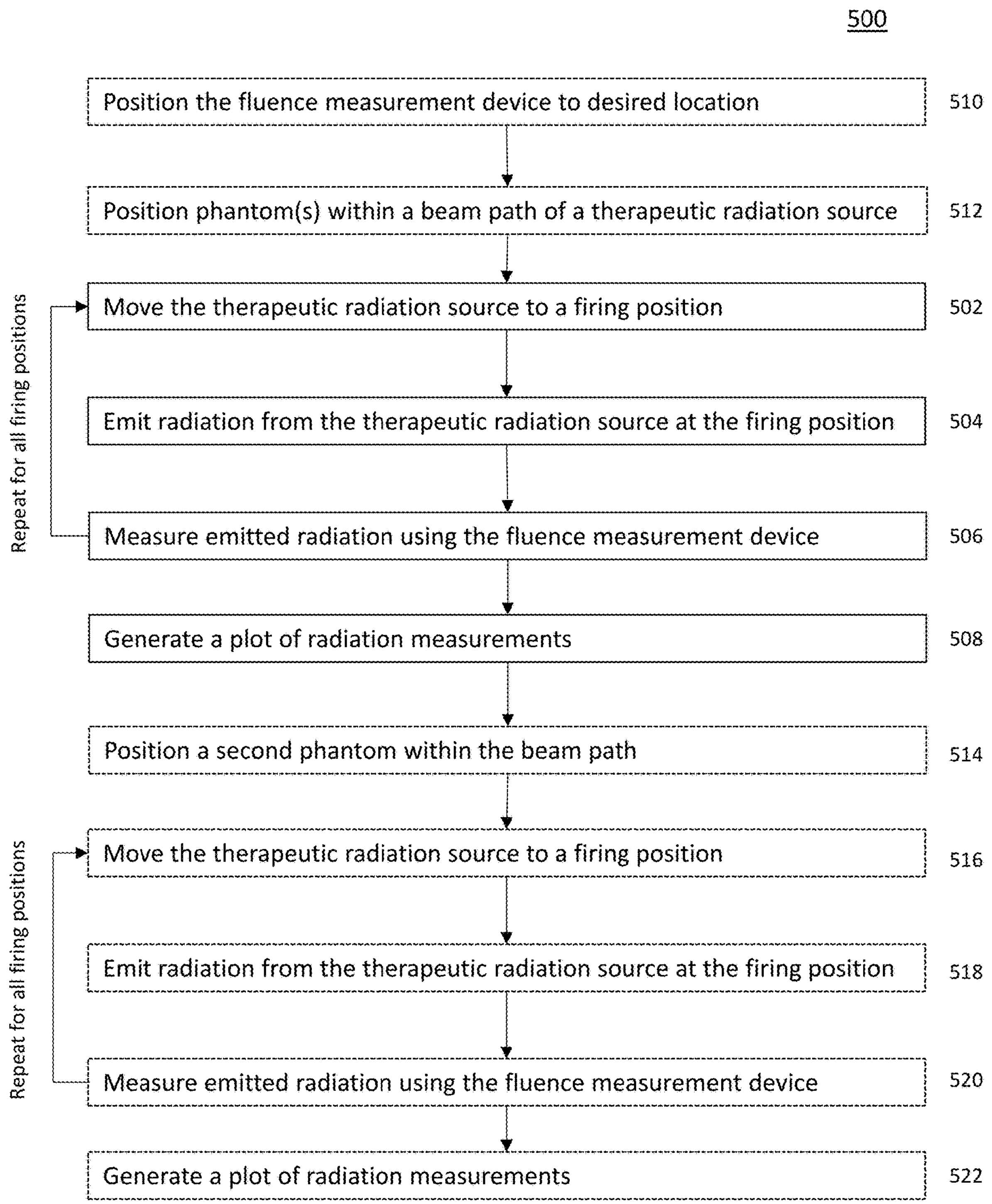
FIG. 5 depicts a flowchart representation of one variation of a method for generating a plot that represents the measured radiation at each firing position.

FIG. 5 depicts a flowchart representation of one variation of a method for generating a plot that represents the measured radiation at each firing position. The generated plot may be used to evaluate the quality (e.g., homogeneity, alignment, shape, etc.) of the radiation beam emitted by the therapeutic radiation source. Method (500) may comprise moving (502) the therapeutic radiation source to a firing position, emitting (504) radiation from the therapeutic radiation source while at the firing position, and measuring (506) emitted radiation using the fluence measurement device. These steps (502-506) may be repeated for all desired firing positions. Method (500) may comprise generating (508) a plot of radiation measurements that includes radiation fluence measurements from the fluence measurement device for each of the firing positions. The data in this generated plot may be used to characterize the properties of the radiation emitted by the therapeutic radiation source. Method (500) may optionally comprise positioning (510) the fluence measurement device to the desired location before the acquiring measurements of emitted radiation. For example, the fluence measurement device may be positioned at any of the locations described above such that outside the entrance irradiation field but within the exit irradiation field. The fluence measurement device may be attached to the housing using any of the movable mounts described above. Optionally, method (500) may comprise positioning (512) a phantom within a beam path of a therapeutic radiation source. For example, the phantom may be placed on the patient platform which may then be advanced into the patient area of the bore. The generated plot may contain radiation fluence data that represents how the presence of the phantom affected and/or changed the characteristics of the radiation emitted by the therapeutic radiation source.

One variation of method (500) may optionally comprise positioning (514) a second phantom within the beam path. For example, the second phantom may be placed in the bore, in the patient area of the bore, and/or placed on the patient platform and moved into the desired position by advancing the patient platform. In some variations, the first phantom may be replaced with the second phantom (i.e., the first phantom is removed) while in other variations, the first phantom may remain in place and the second phantom is added. Method (500) may comprise moving (516) the therapeutic radiation source to a firing position, emitting (518) radiation from the therapeutic radiation source while at the firing position, and measuring (520) emitted radiation using the fluence measurement device. These steps (516-520) may be repeated for all desired firing positions. Method (500) may comprise generating (522) a plot of radiation measurements that includes radiation fluence measurements from the fluence measurement device for each of the firing positions with the second phantom in the bore. The data in this generated plot may be used to characterize the effects of the one or more phantoms on the radiation emitted by the therapeutic radiation source.

Figure 6:
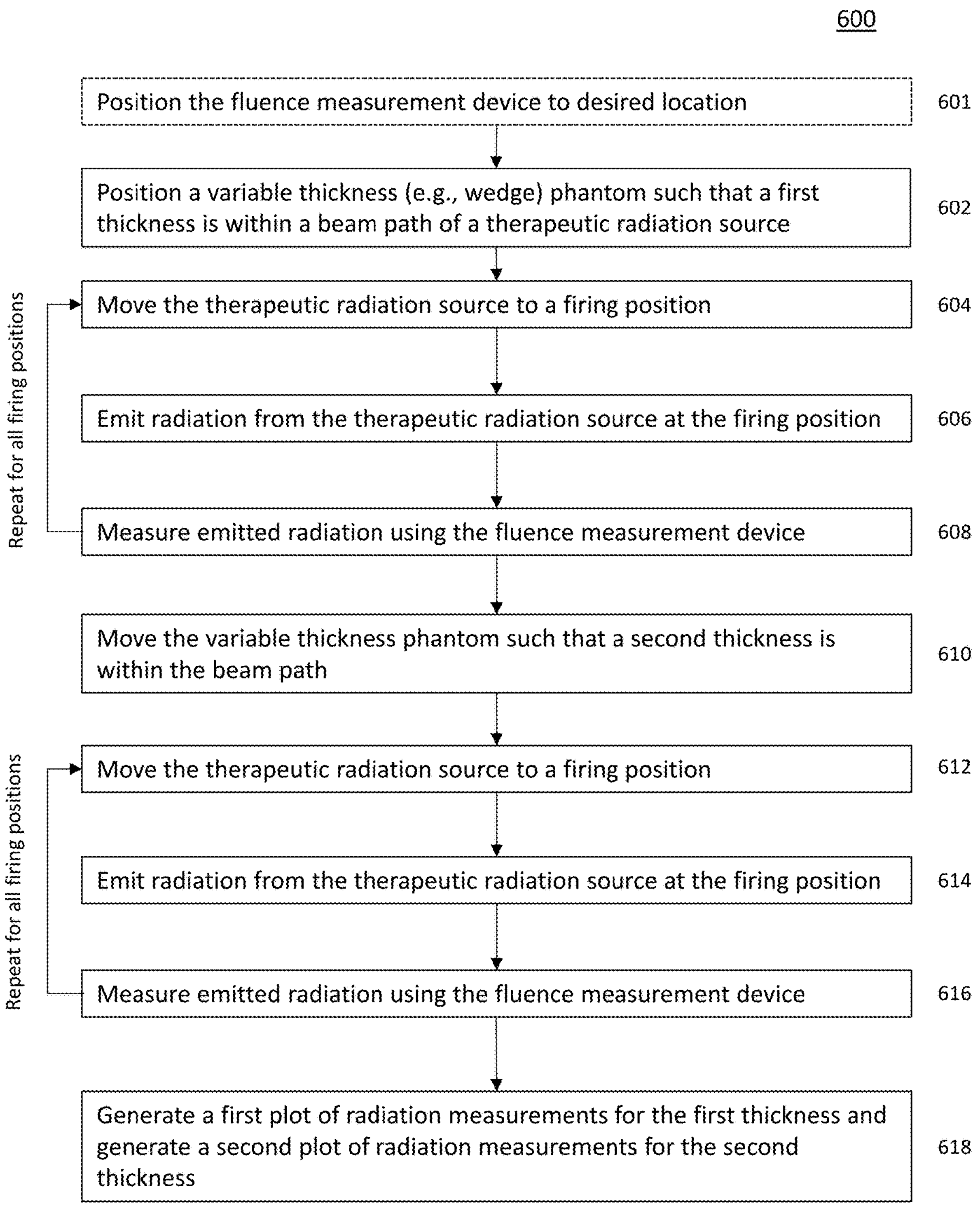
FIG. 6 depicts a flowchart representation of one variation of a method for generating a plot that represents the measured radiation at each firing position with a phantom within a beam path.

FIG. 6 depicts a variation of a method for generating a plot that represents the measured radiation at each firing position with a phantom within the beam path (i.e., within the bore, patient area of the bore). The phantom may have regions of different thickness and/or material properties (e.g., with varying radiation absorption characteristics) and its position within the patient area may be changed so that different regions are within the radiation beam. By collecting radiation fluence data across different phantom properties, plots may be generated that represent the effect of certain phantom properties on radiation absorption and/or delivered dose. For example, a phantom may be selected to have radiation absorption and/or scattering characteristics that aim to mimic a human body. The radiation fluence data acquired during a QA procedure using this phantom may help refine and/or improve the accuracy of dose calculation methods. Clinicians may then have a more accurate measurement of the amount of dose delivered to a target region within a patient. In some variations, a phantom may be a wedge-shaped phantom with regions of different thicknesses. Method (600) may comprise positioning (602) a variable thickness (e.g., wedge) phantom such that a first thickness is within a beam path of a therapeutic radiation source, moving (604) the therapeutic radiation source to a firing position, emitting (606) radiation from the therapeutic radiation source while at the firing position, and measuring (608) emitted radiation using the fluence measurement device. These steps (604-608) may be repeated for all desired firing positions. The radiation fluence measurements from the fluence measurement device for each of the firing positions with the phantom at the first thickness may be stored in a machine-readable memory of the system controller. Method (600) may optionally comprise positioning (601) the fluence measurement device to desired location within the bore, as described previously. Method (600) may comprise moving (610) the variable thickness phantom such that a second thickness is within the beam path, moving (612) the therapeutic radiation source to a firing position, emitting (614) radiation from the therapeutic radiation source while at the firing position, and measuring (616) emitted radiation using the fluence measurement device. These steps (612-616) may be repeated for all desired firing positions. Method (600) may comprise generating (618) a first plot of radiation measurements for the first thickness and generating a second plot of radiation measurements for the second thickness. Any portion of method (600) may be repeated for any number of phantom thicknesses and/or phantoms comprising different material properties.

Figure 7:
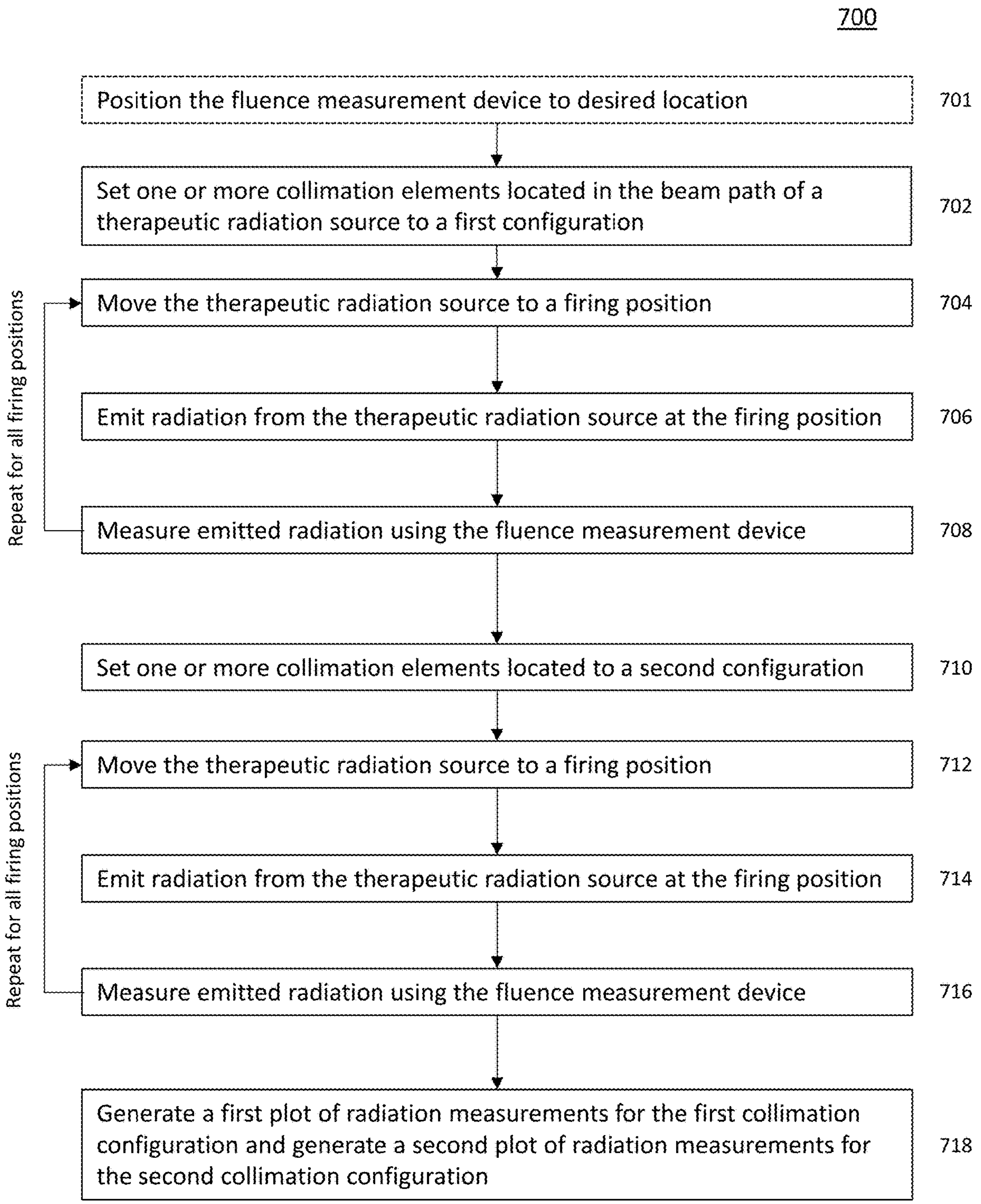
FIG. 7 depicts a flowchart representation of one variation of a method for generating a plot that represents the measured radiation at each firing position for different beam-shaping assembly configurations.

The characteristics of radiation emitted by the therapeutic radiation source may also vary depending on the configuration(s) of the beam-shaping assembly. Some methods for QA of the therapeutic radiation source beam may comprise acquiring radiation fluence measurements using the fluence measurement device(s) coupled to the system housing for different configurations of the beam-shaping assembly. FIG. 7 depicts a variation of a method for generating a plot that represents the measured radiation at each firing position for different beam-shaping assembly configurations. A beam-shaping assembly may comprise one or more jaws where the aperture between the jaws may be adjusted, and one or more multi-leaf collimators (MLCs). The MLC may be a 1-D (i.e., binary) MLC or a 2-D MLC. The MLC leaves and jaws may be referred to as collimation elements. The configurations of the MLC leaves and/or the jaw aperture(s) may be changed, and by collecting radiation fluence data for different configurations of the beam-shaping assembly, plots may be generated that represent the effect of beam-shaping on the characteristics of the emitted radiation and/or delivered dose. The radiation fluence data acquired during a QA procedure that varies the beam-shaping assembly configuration may help refine and/or improve the accuracy of dose calculation methods. Method (700) may comprise setting (702) one or more collimation elements located in the beam path of a therapeutic radiation source to a first configuration, moving (704) the therapeutic radiation source to a firing position, emitting (706) radiation from the therapeutic radiation source while at the firing position, and measuring (708) emitted radiation using the fluence measurement device. These steps (704-708) may be repeated for all desired firing positions. The radiation fluence measurements from the fluence measurement device for each of the firing positions for this first configuration of the beam-shaping assembly may be stored in a machine-readable memory of the system controller. Method (700) may optionally comprise positioning (701) the fluence measurement device to desired location within the bore, as described previously. Method (700) may comprise setting (710) the one or more collimation elements located to a second configuration, moving (712) the therapeutic radiation source to a firing position, emitting (714) radiation from the therapeutic radiation source while at the firing position, and measuring (716) emitted radiation using the fluence measurement device. These steps (712-716) may be repeated for all desired firing positions. Method (700) may comprise generating (718) a first plot of radiation measurements for the first beam-shaping assembly configuration and generating a second plot of radiation measurements for the second beam-shaping assembly configuration. Any portion of method (700) may be repeated for any number of beam-shaping assembly configurations, for example, changing jaw aperture widths, moving the MLC leaves to different positions along their travel path (e.g., opening or closing certain MLC leaves of a binary MLC).

Figure 8:
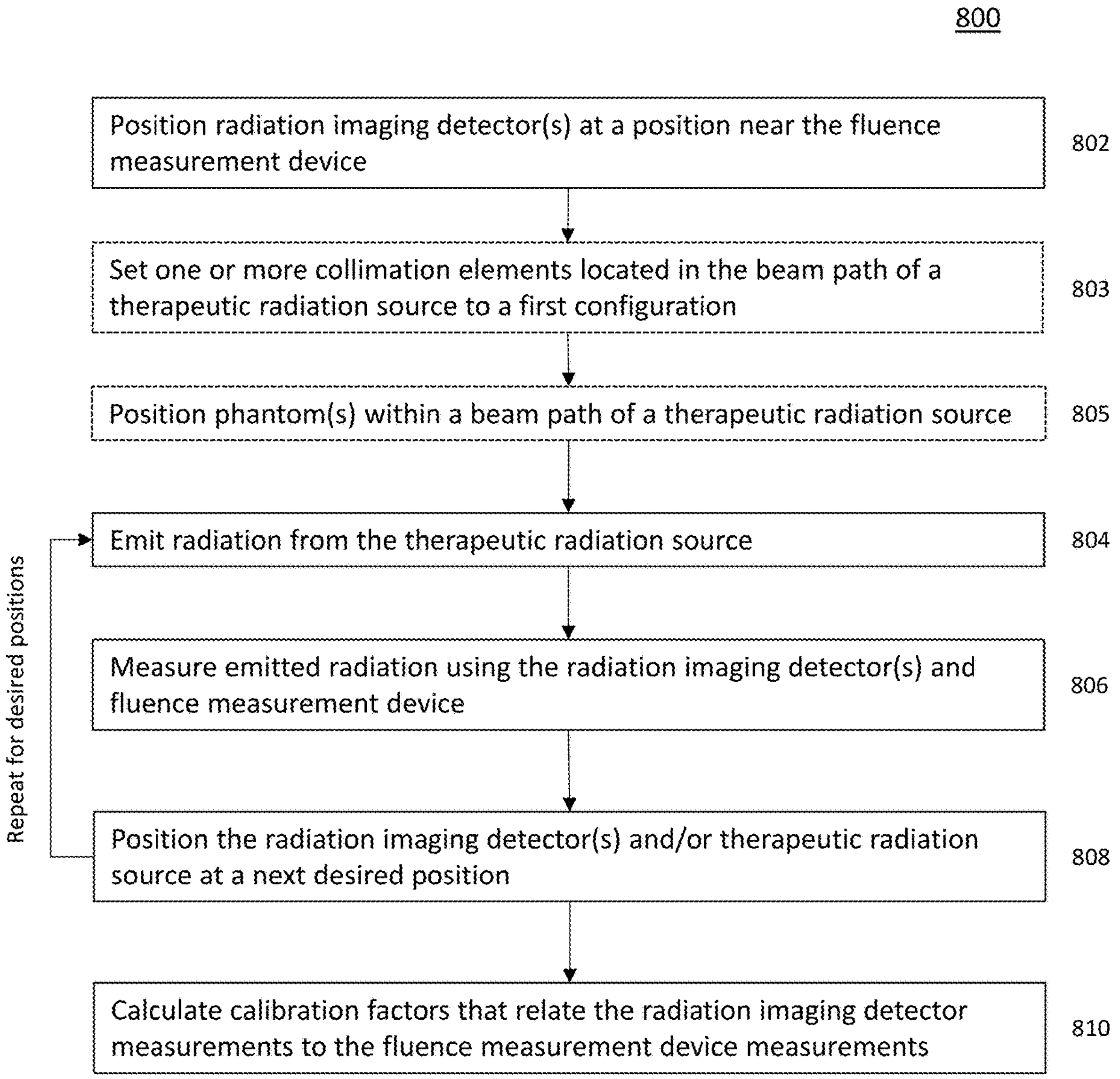
FIG. 8 depicts a flowchart representation of one variation of a method for calibrating an MV detector using a radiation fluence data acquired by a fluence measurement device that is coupled to any of the radiotherapy systems described herein.

Some methods may use the radiation fluence measurements from a fluence measurement device coupled to a radiotherapy system housing (such as any of the systems described herein) to calibrate the MV detector measurements with the fluence measurement device measurements. A calibration procedure may comprise acquiring radiation measurements from both the MV detector and the fluence measurement device coupled to the system housing for the same radiation beam emitted by the therapeutic radiation source and calculating one or more calibration factors using a plurality of these dual radiation measurements. The calibration factor(s) may be used to convert MV detector readings to fluence measurement device readings and vice versa. FIG. 8 depicts one variation of a method for calibrating an MV detector using a radiation fluence data acquired by a fluence measurement device that is coupled to the system housing (i.e., any of the radiotherapy systems described herein). Method (800) may comprise positioning (802) a radiation imaging detector (e.g., MV detector) at a (first) position near the fluence measurement device, emitting (804) radiation from the therapeutic radiation source, measuring (806) emitted radiation using the radiation imaging detector(s) and fluence measurement device, and positioning (808) the radiation imaging detector(s) and/or therapeutic radiation source at a next desired position. These steps (804-808) may be repeated for all desired positions of the radiation imaging detector(s). In some variations, the steps (804-808) may be repeated for 3 or more positions of the radiation imaging detector(s). Method (800) may comprise calculating (810) the one or more calibration factors that relate the radiation imaging detector measurements to the fluence measurement device measurements. In some variations, a correction factor (k) that accounts for the difference between the location of the fluence measurement device and the MV detector may be included. In one variation, a calibration factor (C) may be calculated based on the imaging detector measurement ($Meas_{imag\_detector}$) and the fluence measurement device measurement ($Meas_{fluence\_device}$) as follows:

$$Meas_{fluence_{device}} * k = Meas_{imag_{detector}} * C$$

$$C = \frac{Meas_{fluence_{device}} * k}{Meas_{imag_{detector}}}$$

In some variations, a calibration factor (C) may be calculated for each pixel of the MV detector. The calibration factor(s) may be stored in machine-readable memories of the radiotherapy system controller. In some variations, positioning (808) the radiation imaging detector(s) and/or therapeutic radiation source may comprise rotating a circular gantry (to which the MV detector and therapeutic radiation source are mounted) to move the MV detector and linac to a different firing position while keeping the fluence measurement device stationary. The gantry may be continuously rotated (e.g., at a rate that is slower than in a treatment session), and/or may be rotated in steps. In this fashion, the fluence measurement device may acquire radiation measurements at different portions of the radiation beam along the X-axis (e.g., IEC-X). Alternatively, in other variations, instead of moving the radiation imaging detector(s) and/or therapeutic radiation source, the method may comprise moving the fluence measurement device along the housing while keeping the radiation imaging detector(s) and therapeutic radiation source stationary, and acquiring fluence measurements at each different location of the fluence measurement device. Method (800) may also be used to calibrate other imaging detectors (e.g., PET detectors, CT detectors, MR detectors, etc.) to the fluence measurement device, i.e., calculating calibration factors that map the imaging detector readings and the fluence measurement device readings.

Optionally, some variations may comprise setting (803) one or more collimation elements located in the beam path of a therapeutic radiation source to a first configuration prior to emitting radiation from the therapeutic radiation source.

The steps (804-810) may be repeated for all desired beam-shaping assembly configurations, for example, for multiple irradiation field sizes. In some variations, method (800) may comprise positioning (805) one or more phantoms within a beam path of a therapeutic radiation source. Variations of the method (800) may be used as part of daily quality checks of the radiotherapy system linac, beam-shaping assembly, and/or MV detector.

Figure 9:
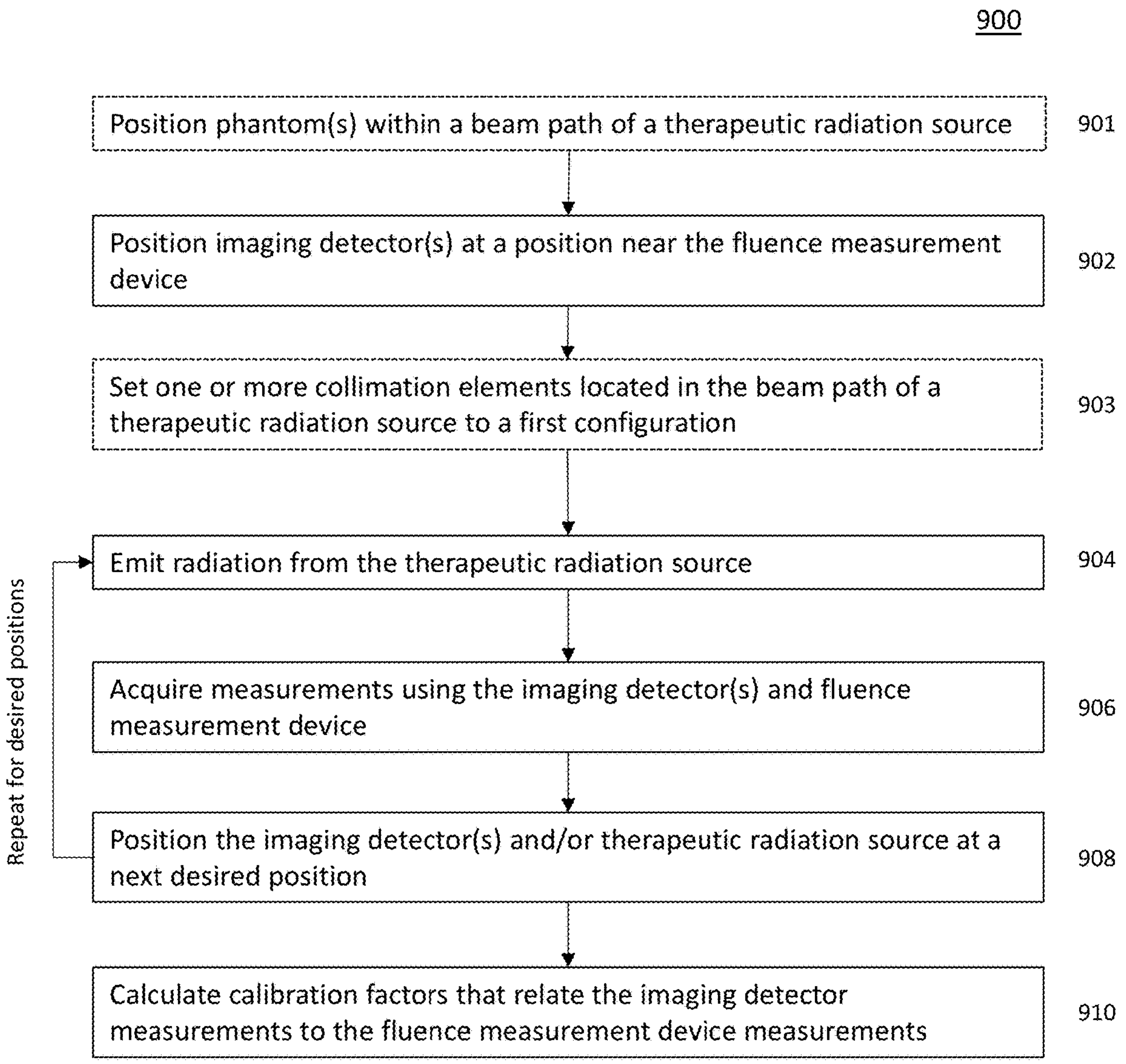
FIG. 9 depicts a flowchart representation of one variation of a method for calibrating imaging detector(s) using a radiation fluence data acquired by a fluence measurement device that is coupled to any of the radiotherapy systems described herein.

Some methods may use the radiation fluence measurements from a fluence measurement device coupled to a radiotherapy system housing (such as any of the systems described herein) to calibrate imaging detector measurements with the fluence measurement device measurements. Imaging detectors may comprise PET detectors, X-ray detectors, etc. For example, some radiotherapy systems may comprise PET detectors that are in-plane with the therapeutic radiation source and MV detector, and it may be desirable to calibrate the PET detector measurements with the fluence measurement device measurements. Alternatively, or additionally, radiotherapy systems may comprise a CT imaging system (which may be in-plane with the therapeutic radiation source or non-coplanar with the therapeutic radiation source), and it may be desirable to calibrate the CT system measurements with the fluence measurement device measurements. In some variations, a phantom may be placed in the patient area and may comprise materials and be sized and shaped to mimic the radiation scattering effects of a human body. The scattered radiation may then be measured by both the imaging detectors (e.g., PET detectors) and the fluence measurement devices. This scattered radiation data may be used to help reduce or remove imaging artifacts caused by scattered radiation during a patient imaging and/or treatment session. FIG. 9 depicts one variation of a method for calibrating imaging detector(s) using a radiation fluence data acquired by a fluence measurement device that is coupled to the system housing (i.e., any of the radiotherapy systems described herein). Method (900) may comprise positioning (902) one or more imaging detectors (e.g., PET detectors, CT detectors, MV detectors, etc.) at a (first) position near the fluence measurement device, emitting (904) radiation from the therapeutic radiation source, measuring (906) emitted radiation using the imaging detector(s) and fluence measurement device, and positioning (908) the imaging detector(s) and/or therapeutic radiation source at a next desired position. These steps (904-908) may be repeated for all desired positions of the imaging detector(s). In some variations, the steps (904-908) may be repeated for 3 or more positions of the radiation imaging detector(s). Method (900) may comprise calculating (910) the one or more calibration factors that relate the imaging detector measurements to the fluence measurement device measurements. In some variations, a correction factor (k) that accounts for the difference between the location of the fluence measurement device and the imaging detectors may be included. In one variation, a calibration factor (C) may be calculated based on the imaging detector measurement ($Meas_{imag\_detector}$) and the fluence measurement device measurement ($Meas_{fluence\_device}$) as follows:

$$Meas_{fluence_{device}} * k = Meas_{imag_{detector}} * C$$

$$C = \frac{Meas_{fluence_{device}} * k}{Meas_{imag_{detector}}}$$

The calibration factor(s) may be stored in machine-readable memories of the radiotherapy system controller. In some variations, positioning (908) the radiation imaging detector(s) and/or therapeutic radiation source may comprise rotating a circular gantry (to which the imaging detectors and therapeutic radiation source are mounted) to move the imaging detectors and linac to a different firing position while keeping the fluence measurement device stationary. The gantry may be continuously rotated (e.g., at a rate that is slower than in a treatment session), and/or may be rotated in steps. In this fashion, the fluence measurement device may acquire radiation measurements at different portions of the radiation beam along the X-axis (e.g., IEC-X), and the imaging detectors may acquire corresponding imaging data. Alternatively, in other variations, instead of moving the imaging detector(s) and/or therapeutic radiation source, the method may comprise moving the fluence measurement device along the housing while keeping the imaging detectors and therapeutic radiation source stationary, and acquiring fluence measurements at each different location of the fluence measurement device.

Optionally, some variations may comprise positioning (801) one or more phantoms within a beam path of a therapeutic radiation source. As described above, the phantom may mimic the radiation scattering properties of a human body. The scattered radiation may be measured by both the imaging detectors and the fluence measurement device, which may be calibrated to each other as described above. Alternatively, or additionally, the measurements of the scattered radiation from the imaging detectors and/or fluence measurement device may be used in imaging noise reduction or removal methods. In some variations, method (900) may comprise setting (903) one or more collimation elements located in the beam path of a therapeutic radiation source to a first configuration prior to emitting radiation from the therapeutic radiation source. The steps (904-910) may be repeated for all desired beam-shaping assembly configurations.

The radiation fluence measurements acquired by the fluence measurement devices in any of the methods described herein may be used to generate a model of the therapeutic radiation beam. In one variation, coefficients of a mathematical fit or model of the radiation beam may be calculated using the fluence measurements of different regions of the radiation beam. For example, if the beam shape is a polynomial function such as $Y=Ax^2+Bx+C$, the coefficients A, B, C may be calculated using multiple fluence measurements from the fluence measurement device for different regions of the radiation beam. Once the coefficients for this model are calculated, this function may be used to calibrate other imaging detectors (e.g., MV, CT, PET detectors). The readings from the other imaging detectors may be mapped to the function $Y=Ax^2+Bx+C$, where the coefficients A, B, C are known, and a calibration factor (C) may be calculated. With the calibration factor (C), future measurements from the imaging detectors may be multiplied by the calibration factor to obtain the true radiation fluence value. In some variations, a calibration factor (C) may be calculated for each pixel of the imaging detector(s).

The methods described above and depicted in FIGS. 8-9 may be used to calculate calibration factor(s) for an imaging detector (e.g., PET detectors, CT detectors, MV detectors, etc.), which may itself be calibrated to another imaging detector. For example, a first calibration factor ($C_1$) may be calculated between a first imaging detector and the fluence measurement device(s) coupled to the system housing. The first imaging detector may be calibrated to a second imaging detector with a second calibration factor ($C_2$). Because the first imaging detector is calibrated to the fluence measurement device(s), the measurements from the second imaging detector may be mapped to the fluence measurement device (s) measurements using the first and second calibration factors. For example, the measurements from first imaging detector ($Meas_{imag_{detector1}}$) may be calibrated to the measurements of the fluence measurement device ($Meas_{fluence_{device}}$) with an optional scaling factor (k):

$$Meas_{fluence_{device}} * k = Meas_{imag_{detector1}} * C_1$$

$$C_1 = \frac{Meas_{fluence_{device}} * k}{Meas_{imag_{detector1}}}$$

The measurements from first imaging detector ($Meas_{imag_{detector1}}$) may be calibrated to the measurements of the second imaging detector ($Meas_{imag_{detector2}}$) with an optional scaling factor (l):

$$Meas_{imag_{detector1}} * l = Meas_{imag_{detector2}} * C_2$$

$$C_2 = \frac{Meas_{imag_{detector1}} * l}{Meas_{imag_{detector2}}}$$

Once the first and second calibration factors are determined, for future measurements of the fluence measurement device may be mapped to the measurements of the second imaging detector, i.e., the second imaging detector and the fluence measurement device may be cross-calibrated:

$$Meas_{fluence_{device}} * k = Meas_{imag_{detector1}} * C_1$$

$$Meas_{fluence_{device}} = \frac{Meas_{imag_{detector2}} * C_2}{k * l} * C_1$$

$$Meas_{fluence_{device}} = Meas_{imag_{detector2}} * C_{cross}, \text{ where } C_{cross} = \frac{C_2 * C_1}{k * l}$$

The calibration factors between two imaging detectors (which may be calibrated relative to each other) and the calibration between the imaging detectors and the fluence measurement devices (which may be directly calibrated to the fluence measurement device or may be cross-calibrated to the fluence measurement device) may be checked using measurements acquired by the fluence measurement devices in the course of a treatment day and/or over multiple QA procedures. Since the fluence measurement devices are coupled to the system housing, they are regularly collecting radiation fluence measurements during all treatment sessions, QA procedures, imaging sessions, etc., there is a large quantity of current data that may be used to tune (e.g., update) calibration factors more frequently than a radiotherapy system without fluence measurement devices coupled to the housing.

Figure 10A:
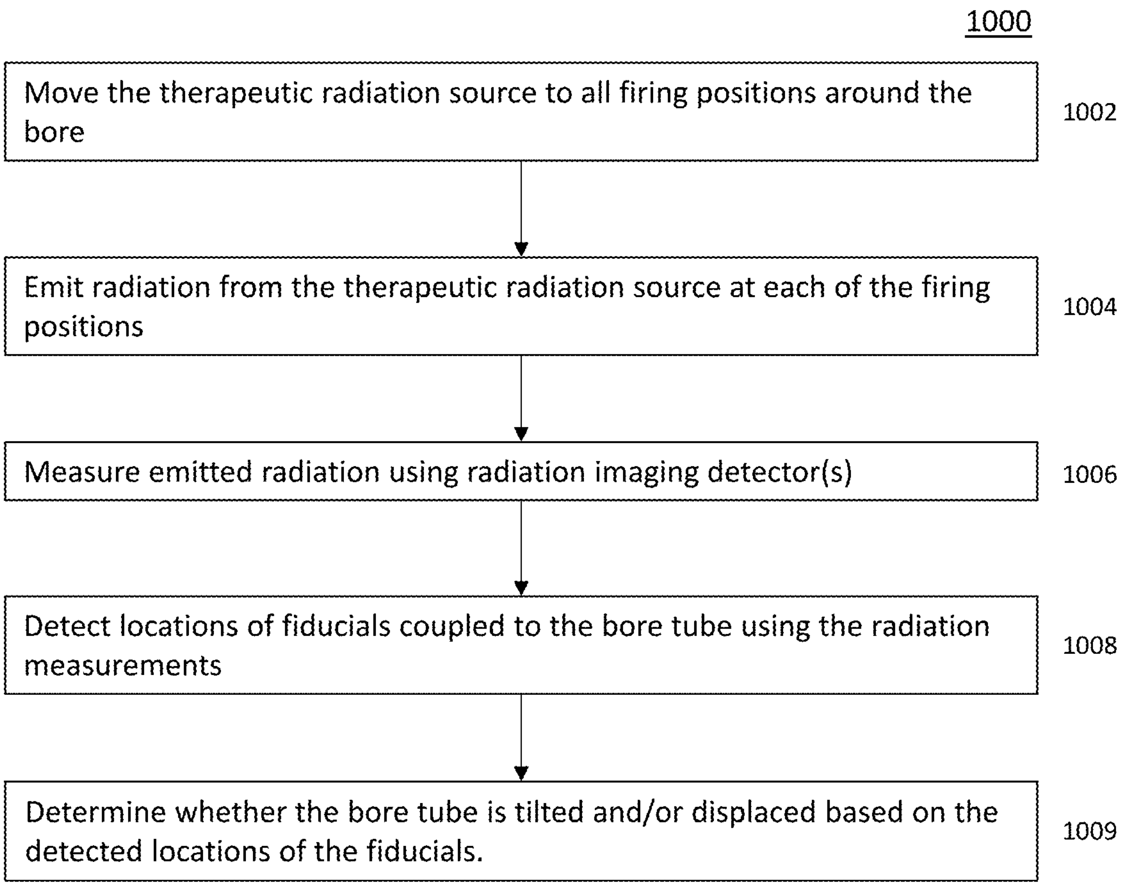
FIG. 10A depicts a flowchart representation of one variation of a method for determining the position of the bore tube.
Figure 10B:
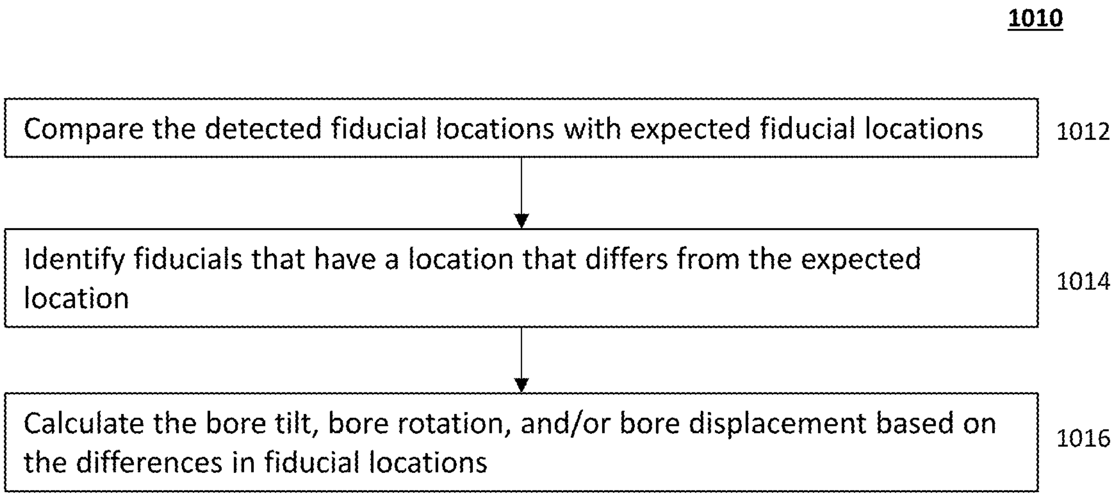
FIG. 10B depicts a flowchart representation of one variation of a method for determining whether a radiotherapy system bore tube is tilted and/or displaced.

A radiotherapy system comprising one or more radioactive and/or radiopaque fiducials coupled to the housing (such as any of those described herein) may also be used in methods that use the fiducials to determine whether the bore tube position is correct, and/or whether bore tube and the gantry-mounted components, as well as the gantry, are in a specified alignment. For example, methods may be used to monitor the bore tube position during a treatment session, imaging session, and/or QA procedure. These methods may be used with a radiotherapy system that may or may not include a fluence measurement device coupled to the housing. FIG. 10A depicts one variation of a method (1000) for determining the position of the bore tube using radiopaque fiducials coupled to the system housing. Method (1000) may comprise moving (1002) the therapeutic radiation source to all firing positions around the bore, emitting (1004) radiation from the therapeutic radiation source at each of the firing positions, measuring (1006) mitted radiation using radiation imaging detector(s), detecting (1008) locations of fiducials coupled to the bore tube using the radiation measurements, and determining (1009) whether the bore tube is tilted and/or displaced based on the detected locations of the fiducials. The radiation imaging detector may be an MV detector. The detected locations of the fiducials may be compared with their expected locations and a deviation outside of an acceptable tolerance may trigger the radiotherapy system to generate a notification to the operator. One variation of a method for determining (1010) whether the bore tube is tilted and/or displaced is depicted in FIG. 10B. Method (1010) may comprise comparing (1012) the detected fiducial locations with expected fiducial locations, identifying (1014) fiducials that have a location that differs from the expected location beyond an acceptable tolerance, and calculating (1016) the bore tilt, bore rotation, and/or bore displacement based on the differences in fiducial locations. In one variation, the radiopaque fiducials may be located just inside the edge of the exit irradiation field, and any bore tube tilting or displacement would cause the radiopaque fiducials to disappear from the MV detector measurements. In another variation, the radiopaque fiducials may be located just outside the edge of the exit irradiation field, and any bore tube tilting or displacement would cause the radiopaque fiducials to appear in the MV detector measurements. In some variations, the detected locations of the fiducials may be used to verify the location of the fluence measurement device and/or determine the correct angle from which radiation was fired. Alternatively, or additionally, the detected locations of the fiducials may be used to verify the relative position of the collimation components (i.e., beam-shaping assembly), such as the jaws or the MLC(s).

Figure 11:
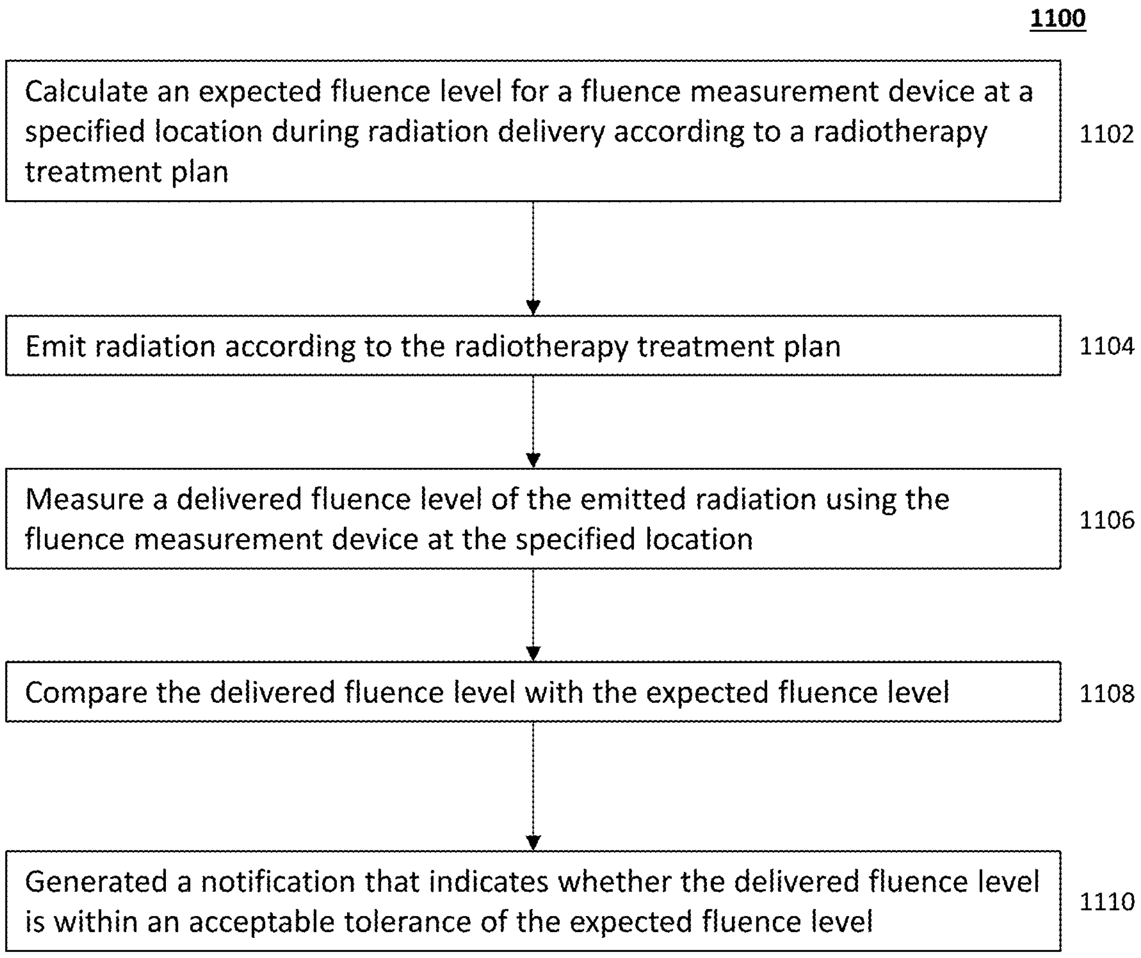
FIG. 11 depicts a flowchart representation of one variation of a method for evaluating the quality of a radiation delivery session (with or without a patient in the patient area).

A radiotherapy system comprising one or more fluence measurement devices coupled to the housing (such as any of those described herein) may also be used in methods for monitoring the delivery of radiation to the patient area. In some variations, the fluence measurement device(s) may be used to measure the amount of radiation delivered to a patient. Alternatively, the fluence measurement device(s) may be used to measure the amount of radiation delivered to a phantom (in the absence of a patient). The data from the fluence measurement device may be used to evaluate the quality of a radiation delivery and whether the delivery was according to the treatment plan. FIG. 11 depicts one variation of a method for evaluating the quality of a radiation delivery session (with or without a patient in the patient area). Method (1100) may comprise calculating (1102) an expected fluence level for a fluence measurement device at a specified location during radiation delivery according to a radiotherapy treatment plan, emitting (1104) radiation according to the radiotherapy treatment plan, measuring (1106) a delivered fluence level of the emitted radiation using the fluence measurement device at the specified location, comparing (1108) the delivered fluence level with the expected fluence level, and generating (1110) a notification that indicates whether the delivered fluence level is within an acceptable tolerance of the expected fluence level. The measurements of the delivered fluence level may be cumulative over an entire radiation emission session (e.g., treatment session, imaging session, QA procedure). The comparison of the expected cumulative radiation delivery with the actual cumulative radiation delivery may help determine whether the radiotherapy system is operating as intended. Method (1100) may be used with a radiotherapy system comprising one fluence measurement device, or may be used with a radiotherapy system comprising two or more fluence measurement devices. For example, method (110) may optionally comprise calculating a second expected fluence level for a second fluence measurement device at a second specified location during radiation delivery according to a radiotherapy treatment plan, measuring a second delivered fluence level of the emitted radiation using the second fluence measurement at the second specified location, comparing the second delivered fluence level with the second expected fluence level, and generating a notification that indicated whether the second delivered fluence level is within an acceptable tolerance of the second expected fluence level.

As described above, the fluence measurement device may be used to calibrate the MV detector (e.g., using any calibration method, such as the calibration methods described herein), and methods for monitoring or evaluating radiation delivery may comprise calculating the delivered radiation dose during the delivery session using the data acquired on the calibrated MV detector. The calculated delivered radiation dose may be compared with the planned radiation dose during the delivery session and notifications may be generated during the session (and/or after) to alert the system operator if the delivered dose deviates substantially from the planned dose. The radiation delivery session may be a QA or calibration session without a patient on the platform, or may be treatment session with a patient on the platform. In one variation, a method for generating a radiation dose image may comprise emitting radiation (e.g., therapeutic radiation) while the patient platform is stopped at one of a series of patient platform positions (also referred to as beam stations), acquiring MV detector data from a calibrated MV detector, and generating a radiation dose field and/or a sinogram using the MV detector data. This may be performed on a beam station-by-beam station basis, where one radiation dose field and/or sinogram is generated for each beam station. The radiation dose field and/or sinogram may be compared to a planned radiation dose field and/or sinogram, and in some variations, a visual and/or audible notification may be generated to indicate whether the calculated radiation dose field and/or sinogram is substantially similar to (or different from) the planned radiation dose field and/or sinogram. In some variations, the comparison between the calculated and the planned radiation dose fields and/or sinograms may be performed for each beam station before the patient platform is moved to the next beam station. A radiation dose field may be a 2-D (e.g., X-axis, Y-axis in space) or 3-D plot (e.g., X-axis, Y-axis, Z-axis in space) where the intensity at each point represents the dose value at that point. A sinogram may be a plot having one axis representing a detection angle and a second axis representing an MV detector image. One or more of these dose representations may be used to monitor the delivery of radiation to the patient area.

While different variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the example inventions described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive variations described herein. It is, therefore, to be understood that the foregoing variations are presented by way of example only and that, within the scope of the appended claims and equivalents thereto; inventive variations may be practiced otherwise than as specifically described and claimed. Inventive aspects may include one or more of the individual features, systems, articles, materials, kits, and/or methods described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described systems and methods can be implemented in any of numerous ways. For example, at least some methods of the present technology may be implemented using hardware, firmware, software, or a combination thereof. When implemented in firmware and/or software, the firmware and/or software code can be executed on any suitable processor or collection of logic components, whether provided in a single device or distributed among multiple devices.

In this respect, various aspects described herein may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various examples of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of example inventions as discussed above. Additionally, it should be appreciated that according to one aspect, one or more computer programs that when executed perform methods of the present invention need not reside on a single computer or processor but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in different variations.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, variations of the invention may be constructed in which acts are performed in an order different than illustrated, which may include performing some acts simultaneously, even though shown as sequential acts in illustrative variations and examples.

The invention claimed is:

1. A radiotherapy system comprising:
- a gantry that is rotatable about a patient area;
- a therapeutic radiation source mounted on the rotatable gantry;
- a housing disposed over the rotatable gantry;
- a radiation fluence measurement device that is coupled to a surface of the housing;
- a bore defined by the housing surface and having a longitudinal axis, wherein the therapeutic radiation source is located at a first position along the longitudinal axis and the radiation fluence measurement device is located at a second position along the longitudinal axis at an offset distance from the first position; and
- a radiopaque fiducial coupled to the housing surface.

2. The system of claim 1, wherein the radiation fluence measurement device is movable independently of the therapeutic radiation source.

3. The system of claim 1, wherein the radiation fluence measurement device is movable along the housing surface.

4. The system of claim 3, wherein the radiation fluence measurement device is laterally movable along the housing surface.

5. The system of claim 1, wherein the radiation fluence measurement device is in a fixed location along the housing surface.

6. The system of claim 1, wherein the radiation fluence measurement device is located on the housing surface such that it measures radiation exiting the patient area.

7. The system of claim 6, wherein the radiation fluence measurement device is located on the housing surface such that it does not interfere with a therapeutic radiation beam directed at the patient area.

8. The system of claim 1, further comprising a bore defined by the housing surface and having a longitudinal axis, wherein the radiation fluence measurement device is offset from the therapeutic radiation source along the longitudinal axis.

9. The system of claim 1, wherein the offset distance is at least 0.4 cm.

10. The system of claim 9, wherein the offset distance is at least 0.5 cm.

11. The system of claim 10, wherein the offset distance is at least 0.7 cm.

12. The system of claim 11, wherein the offset distance is at least 0.8 cm.

13. The system of claim 1, wherein the offset distance is greater than or equal to half a radiation field size at the housing surface.

14. The system of claim 1, further comprising a radiation imaging detector mounted on the gantry directly opposite the therapeutic radiation source.

15. The system of claim 1, further comprising an imaging system mounted on the rotatable gantry.

16. The system of claim 15, wherein the imaging system comprises a CT imaging system.

17. The system of claim 15, wherein the imaging system comprises a PET imaging system.

18. The system of claim 1, wherein the radiation fluence measurement device is a first radiation fluence measurement device and wherein the system further comprises a second radiation fluence measurement device.

19. The system of claim 18, wherein the second radiation fluence measurement device is coupled to the housing surface opposite the first radiation fluence measurement device.

20. The system of claim 18, wherein the second radiation fluence measurement device is coupled to the housing surface about 90° from the first radiation fluence measurement device.

21. The system of claim 1, wherein the radiation fluence measurement device is a first radiation fluence measurement device and wherein the system further comprises a second radiation fluence measurement device that is located at a third position along the longitudinal axis at a second offset distance from the first position.

22. The system of claim 21, wherein the second radiation fluence measurement device is axially adjacent to the first radiation fluence measurement device.

23. The system of claim 1, wherein the radiation fluence measurement device comprises one or more of an ion chamber, diode array, dosimetry film, thin film transistor (TFT), thermoluminescent dosimeter (TLD), and/or a dosimeter.

24. The system of claim 1, further comprising a plurality of radiopaque fiducials distributed around a perimeter of the housing surface that defines the bore.

25. The system of claim 24, wherein each of the plurality of radiopaque fiducials is uniquely identifiable from the others.

26. The system of claim 24, wherein the plurality of radiopaque fiducials is distributed around the perimeter of a cross-section of the bore, wherein the cross-section is located at a second offset distance from the first position.

27. The system of claim 26, wherein the second offset distance is at least 0.4 cm.

28. The system of claim 26, wherein the second offset distance is greater than or equal to half a radiation field size at the housing surface.

29. The system of claim 24, wherein the plurality of radiopaque fiducials is located on the housing surface such that it does not interfere with a therapeutic radiation beam directed at the patient area.

30. The system of claim 1, wherein the gantry is continuously rotatable through 360°.

31. The system of claim 1, wherein the radiation fluence measurement device is coupled to a surface of the housing at a location determined based on a radiotherapy treatment plan fluence map.

32. The system of claim 1, wherein the housing comprises a bore tube and the radiation fluence measurement device is coupled to a surface of the bore tube.

33. They system of claim 32, wherein the bore tube has a longitudinal axis and the radiation fluence measurement device is movable along the longitudinal axis.

* * * * *